US008306755B2

(12) United States Patent
Pitman et al.

(10) Patent No.: US 8,306,755 B2
(45) Date of Patent: Nov. 6, 2012

(54) FIELD-BASED SIMILARITY SEARCH SYSTEM AND METHOD

(75) Inventors: Michael C. Pitman, Stamford, CT (US); Blake G. Fitch, White Plains, NY (US); Hans W. Horn, San Jose, CA (US); Wolfgang Huber, Murg-Niederhof (DE); Julia E. Rice, Sunnyvale, CA (US); William C. Swope, Morgan Hill, CA (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 13/113,256

(22) Filed: May 23, 2011

(65) Prior Publication Data

US 2011/0225148 A1  Sep. 15, 2011

Related U.S. Application Data

(62) Division of application No. 12/544,889, filed on Aug. 20, 2009, now Pat. No. 8,014,990, which is a division of application No. 10/102,902, filed on Mar. 22, 2002, now abandoned.

(60) Provisional application No. 60/278,260, filed on Mar. 23, 2001.

(51) Int. Cl.
*G01N 33/48* (2006.01)
*G01N 31/00* (2006.01)
*C12Q 1/00* (2006.01)

(52) U.S. Cl. ................... 702/19; 702/22; 435/4

(58) Field of Classification Search ............ None
See application file for complete search history.

(56) References Cited

U.S. PATENT DOCUMENTS

| 5,331,573 | A | 7/1994 | Balaji et al. |
| 5,784,294 | A | 7/1998 | Platt et al. |
| 5,802,525 | A | 9/1998 | Rigoutsos |
| 6,317,617 | B1 | 11/2001 | Gilhuijs et al. |
| 6,349,265 | B1 | 2/2002 | Pitman et al. |
| 8,014,990 | B2 * | 9/2011 | Pitman et al. ............ 703/12 |

OTHER PUBLICATIONS

Cornilescu et al. Protein backbone angle restraints from searching a database for chemical shift and sequence homology. Journal of Biomolecular NMR, vol. 13, 1999, pp. 289-302.*
Atta-ur-Raman, Nuclear Magnetic Resonance: Basic Principles. Springer-Verlag, New York, 1986, pp. 8-10.*
Pitman et al. U.S. Appl. No. 09/275,568, "Similarity Searching of Molecules Based Upon Descriptor Vectors Characterizing Molecular Regions," filed Mar. 24, 1999, pp. 1-47.*

(Continued)

*Primary Examiner* — Russell S Negin
(74) *Attorney, Agent, or Firm* — Daniel P. Morris; McGinn IP Law Group, PLLC

(57) ABSTRACT

A similarity search method includes generating a feature database which stores data pertaining to a candidate molecule, as executed by a processor of a computer, the database including a hash table having entries which are generated based on, a set of descriptors generated from conformations of fragment graphs of the candidate molecule, the fragment graphs including plural fragment nodes connected by rotatable bond edges, a specific conformation of the fragment node including a fragment of the candidate molecule, and two neighboring fragments connected by a rotatable bond at a specific dihedral angle including a fragment pair, and a context-adapted descriptor-to-key mapping which maps the set of descriptors to a set of feature keys including indices that label grid cells in discriminant space.

14 Claims, 19 Drawing Sheets

OTHER PUBLICATIONS

Jan Drenth, Principles of Protein X-ray Crystallography, 1995, pp. 1-18.*

Service RF. Tapping DNA for Structures Produces a Trickle, Science, vol. 298, 2002, pp. 948-950.*

Rigoutsos et al., RC 20497 (90854) 1996, Research Report: Flexible 3D-Substructure Matching & Novel Conformer Derivation in very large databases of 3D molecular information; 33 pages.

Berman et al., Nucleic Acids Research, vol. 28, pp. 235-242, Jan. 2000.

Pearson et al., Proc. Natl. Acad. Sci., vol. 85, pp. 2444-2448, 1998.

Aude et al., Computers & Chemistry, 1999, vol. 23, pp. 303-315.

Rarey et al., Journal of Computer-Aided Molecular Design, vol. 11, pp. 369-384, 1997.

Olson, C.F., Efficient pose clustering suing a randomized algorithm, International Journal of Computer Vision; vol. 23, 1997, pp. 131-147.

* cited by examiner

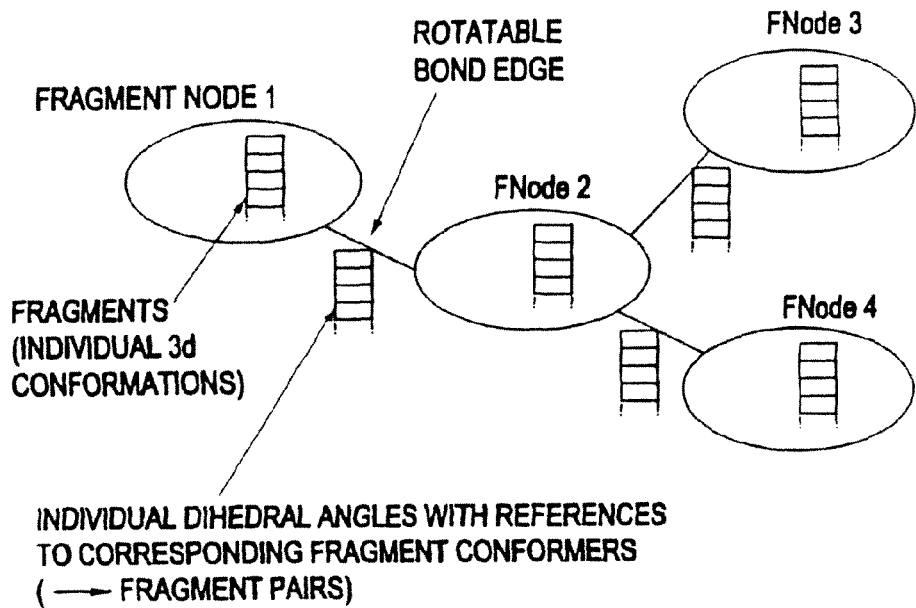

FIG.3

Table I

| | |
|---|---|
| $\|\alpha_1\| \geq \|\alpha_2\| \geq \|\alpha_3\|$ | V is replaced by $(\text{sign}\,\alpha_1 \cdot \vec{v}_1, \text{sign}\,\alpha_2 \cdot \vec{v}_2, s \cdot \vec{v}_3)$ |
| $\|\alpha_1\| \geq \|\alpha_3\| \geq \|\alpha_2\|$ | V is replaced by $(\text{sign}\,\alpha_1 \cdot \vec{v}_1, s \cdot \vec{v}_2, \text{sign}\,\alpha_3 \cdot \vec{v}_3)$ |
| $\|\alpha_2\| \geq \|\alpha_1\| \geq \|\alpha_3\|$ | V is replaced by $(\text{sign}\,\alpha_1 \cdot \vec{v}_1, \text{sign}\,\alpha_2 \cdot \vec{v}_2, s \cdot \vec{v}_3)$ |
| $\|\alpha_2\| \geq \|\alpha_3\| \geq \|\alpha_1\|$ | V is replaced by $(\text{sign}\,\alpha_1 \cdot \vec{v}_1, s \cdot \vec{v}_2, \text{sign}\,\alpha_3 \cdot \vec{v}_3)$ |
| $\|\alpha_3\| \geq \|\alpha_1\| \geq \|\alpha_2\|$ | V is replaced by $(s \cdot \vec{v}_1, \text{sign}\,\alpha_2 \cdot \vec{v}_2, \text{sign}\,\alpha_3 \cdot \vec{v}_3)$ |
| $\|\alpha_3\| \geq \|\alpha_2\| \geq \|\alpha_1\|$ | V is replaced by $(s \cdot \vec{v}_1, \text{sign}\,\alpha_2 \cdot \vec{v}_2, \text{sign}\,\alpha_3 \cdot \vec{v}_3)$ |

FIG.4

Table II

| Quantity | Components |
|---|---|
| Total "mass" $M$ | 1 |
| Total "charge" $Q$ | 1 |
| Sorted eigenvalues $J_1 < J_2 < J_3$ of the inertial tensor $J$ | 3 |
| Dipole vector $V^t \vec{p}$ | 3 |
| Quadrupole tensor $V^t Q V$ | 5 |
| Spatial vector between the centers $V^t(\vec{c}_\mu - \vec{c}_\rho)$ | 3 |

DIHYDROFOLATE

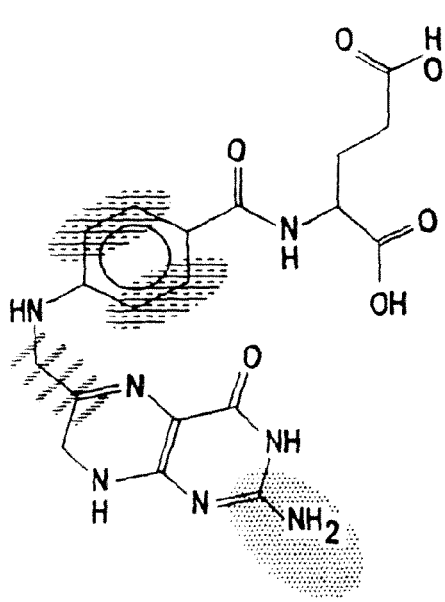

FIG.7A

METHOTREXATE

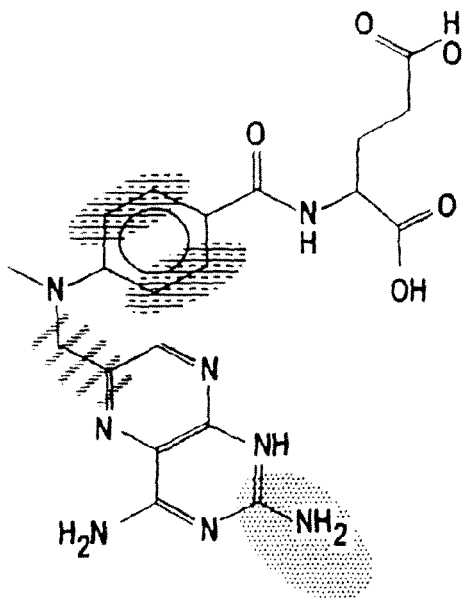

FIG.7B

Table III

| Parameter | Value | See eqn. |
|---|---|---|
| Scoop center placement | Nuclear locations | (9), (11) |
| Scoop radius $R$ | 3 Å | (7), (8) |
| Smearing parameter $\sigma$ | 0.5 Å | (10) |
| Scoop internal grid spacing $\Delta R$ | $R/18$ | |
| Asymmetry threshold for $a_n$ | 0.02 | (22) |
| Degeneracy threshold $e_J$ | 0.04 | (21) |
| Transformation metric parameter $a$ | 3 Å | (27) |
| Cluster distance threshold $d_{clust}$ | 3 Å | |
| Assembly bump check | 1.7 Å | |
| Assembly merge threshold | 3.0 Å | |
| Assembly shape screen | 3.5 Å | |

FIG.8

Table IV

| | | | | | | | | |
|---|---|---|---|---|---|---|---|---|
| | 2O28 2H36 | 1C2 2N3<br>1N3 2O23<br>1O6 2H35<br>1O31<br>1H33 | 1H53<br>1O29 2H50<br>1H52 2H55 | | | | | 1C18 |
| | | 2N1 | | | | | | |
| | 2N11 2H46<br>1N4<br>1C17<br>1C19<br>1C20<br>1O32<br>1H35<br>1H44 | 1O22 2C2<br>1H34 2H34<br>2H37 | 2N6 | 1C12 2H42 | | 2O32 | 2C15 2H54 | 1H48 2O33<br>2H52 |
| | | 1N8 2C5<br>1O28 2C10<br>2H56 | | 1C10 | | 2H43 | 2C9 2C29<br>2H39 | |
| | 1N1 2N4<br>1C5 2N8<br>1C16 2C17<br>1C21 2C18<br>1H41 2C20<br>1H42 2C21<br>1H45 2O27<br>2H44<br>2H45<br>2H47 | 1N11 2H38<br>1N14<br>1N23<br>1H38<br>1H43<br>1H46 | 1H36 | | 2H41 | 1C9 2H40<br>1C26<br>1H37<br>1H50 | 1C13 2C9<br>1H39 2C29<br>1H40 2H39 | 1C25 2C12<br>1C30 2N14<br>1H49 2N24<br>1H51 2C26<br>2C30<br>2C31<br>2H48<br>2H53 |
| | | | | | | | 1C27 2C13<br>2H51 | 1C24 2C25<br>1H47 2H49 |
| 1C15 | 1C7 | | 2C19 | | | | | 2C7<br>2C16<br>2C22 |

FIG.10

Table V

| Votes | Full Correspondence Occurrences | Functional Grouping Occurrences |
|---|---|---|
| 16 | 1 | |
| 11 | 4 | |
| 10 | 1 | |
| 9 | 6 | 1 |
| 8 | 7 | - |
| 7 | 16 | - |
| 6 | 34 | - |
| 5 | 70 | - |
| 4 | 123 | 4 |
| 3 | 272 | 13 |
| 2 | 414 | 27 |
| 1 | 330 | 76 |
| Total Clusters | 1278 | 121 |
| Total Correspondences | 3312 | 194 |

FIG.12

Table VI

| Fragment Node | Fragment Conformers | Rotatable Bond Edge | Number of Fragment Pairs |
|---|---|---|---|
| A | 6 | A-B | 49 |
| B | 2 | B-C | 235 |
| C | 27 | | |
| Total | 35 | Total | 284 |

FIG.13

Table VII

| Votes | Element Grouping Occurrences | Functional Grouping Occurrences |
|---|---|---|
| 11 |  | 14 |
| 10 |  | 9 |
| 9 | 15 | 85 |
| 8 | 126 | 19 |
| 7 | 129 | 43 |
| 6 | 210 | 235 |
| 5 | 410 | 249 |
| 4 | 448 | 600 |
| 3 | 1358 | 1466 |
| 2 | 6635 | 6391 |
| 1 | 31157 | 11340 |
| Total Clusters | 40488 | 20451 |
| Total Correspondences | 55649 | 35037 |

FIG.14

Table VIII

| Assembly Phase | Functional Grouping | Elemental Grouping |
|---|---|---|
| Selected Correspondence Clusters | 654 | 890 |
| Potential Merge Pairs | 91092 | 103128 |
| Actual Merges | 13886 | 25816 |
| After Bump Check | 11194 | 21576 |
| After Shape Screen | 436 | 428 |

FIG.15

Table IX

| PDB Source | Rotatable Bonds | Approximate Conformers Represented | Fragment Conformers | Fragment Pairs | Total Features |
|---|---|---|---|---|---|
| DHFR Inactives | | | | | |
| 1cbx | 3 | 216 | 12 | 103 | 2781 |
| 1tlp | 8 | 1679616 | 54 | 3272 | 138866 |
| 1tmn | 9 | 10077696 | 68 | 2922 | 107601 |
| 3tmn | 4 | 1296 | 28 | 350 | 15050 |
| 5tmn | 8 | 1679616 | 68 | 4219 | 174957 |
| 7cpa | 9 | 10077696 | 144 | 1735 | 82231 |
| 3gpb | 2 | 36 | 6 | 11 | 319 |
| 4gpb | 2 | 36 | 7 | 19 | 532 |
| 4dfr | 5 | 15552 | 35 | 284 | 10185 |
| Total for Inactives | - | 23531760 | 422 | 12915 | 532522 |
| DHFR Inhibitors | | | | | |
| 1 | 2 | 36 | 7 | 21 | 798 |
| 2 | 2 | 36 | 7 | 21 | 756 |
| 4 | 2 | 36 | 4 | 9 | 36 |
| 6 | 3 | 216 | 8 | 53 | 2173 |
| 61 | 3 | 216 | 8 | 55 | 2475 |
| 64 | 3 | 216 | 8 | 51 | 2448 |
| 67 | 2 | 36 | 7 | 21 | 735 |
| 68 | 2 | 36 | 8 | 21 | 714 |
| Total for Inhibitors | - | 828 | 57 | 252 | 10459 |
| Combined Total | - | 23532588 | 479 | 13171 | 542981 |

FIG. 19

Table X
DHFR Inactives

| Cluster Size | 1cbx | 1tlp | 1tmn | 3tmn | 5tmn | 7cpa | 3gpb | 4gpb | 4dfr | Total |
|---|---|---|---|---|---|---|---|---|---|---|
| 11 | - | - | - | - | - | - | - | - | 14 | 14 |
| 10 | - | - | - | - | - | - | - | - | 9 | 9 |
| 9 | - | - | - | - | - | - | - | - | 85 | 85 |
| 8 | - | - | - | - | - | - | - | - | 19 | 19 |
| 7 | - | - | 4 | - | - | 14 | - | - | 43 | 63 |
| 6 | 1 | 15 | 21 | 8 | 2 | 63 | - | - | 235 | 343 |
| 5 | 4 | 1224 | 743 | 194 | 0 | 1887 | - | - | 249 | 4311 |
| 4 | 67 | 4574 | 1590 | 556 | 10 | 3380 | - | - | 600 | 11750 |
| 3 | 245 | 15434 | 10231 | 1592 | 983 | 7947 | - | - | 1466 | 53570 |
| 2 | 1620 | 52362 | 42092 | 4667 | 16655 | 42599 | 41 | 61 | 6391 | 221924 |
| 1 | 5061 | 190624 | 132235 | 22714 | 72091 | 132622 | 225 | 519 | 11340 | 744313 |
| Total Clusters | 6998 | 264233 | 186916 | 29731 | 248973 | 188512 | 266 | 580 | 20451 | 1036401 |
| Total Correspondences | 9330 | 366156 | 257341 | 40066 | 338714 | 265092 | 307 | 641 | 35037 | 1421086 |

FIG.21

Table XI
DHFR Inhibitors

| Cluster Size | 1 | 2 | 4 | 6 | 61 | 64 | 67 | 68 | Total |
|---|---|---|---|---|---|---|---|---|---|
| 7 | - | - | - | 1 | - | 1 | - | - | 2 |
| 6 | 3 | 3 | 5 | 10 | 9 | 13 | 11 | 17 | 71 |
| 5 | 35 | 9 | 7 | 79 | 53 | 60 | 37 | 24 | 304 |
| 4 | 89 | 57 | 25 | 119 | 148 | 115 | 45 | 26 | 624 |
| 3 | 237 | 183 | 89 | 255 | 325 | 252 | 160 | 109 | 1610 |
| 2 | 638 | 559 | 254 | 1226 | 1152 | 1021 | 453 | 477 | 5780 |
| 1 | 1287 | 1319 | 662 | 4022 | 3762 | 3422 | 1248 | 1189 | 16911 |
| Total Clusters | 2289 | 2130 | 1042 | 5712 | 5449 | 4884 | 1954 | 1842 | 25302 |
| Total Correspondences | 3823 | 3277 | 1602 | 8177 | 7952 | 7065 | 3065 | 2796 | 37757 |

FIG.22

Table XII

| PDB Source | Alignment Time, sec | Assembly Time, sec | Initial Alignments | Merges | Candidates | Top Score |
|---|---|---|---|---|---|---|
| 1cbx | 19 | 22 | 1399 | - | 450 | 0.48 |
| 1tlp | 489 | 10 | 1773 | - | - | - |
| 1tmn | 409 | 6 | 1095 | - | - | - |
| 3tmn | 55 | 8 | 690 | - | 81 | 0.66 |
| 5tmn | 571 | 9 | 996 | - | - | - |
| 7cpa | 545 | 15 | 1964 | - | - | - |
| 3gpb | 2 | 7 | 266 | - | 129 | 0.43 |
| 4gpb | 3 | 12 | 580 | - | 180 | 0.42 |
| 4dfr | 48 | 209 | 654 | 13886 | 436 | 0.95 |

FIG. 23

Table XIII

| Compound Number | Alignment Time, sec | Assembly Time, sec | Initial Alignments | Candidates | Top score | ΔG binding [47] (Kcal·mol$^{-1}$) |
|---|---|---|---|---|---|---|
| 1 | 60 | 8 | 1002 | 37 | 0.67 | -5.8 |
| 2 | 50 | 6 | 811 | 26 | 0.65 | -6.0 |
| 4 | 50 | 9 | 1034 | 33 | 0.66 | -6.5 |
| 6 | 75 | 15 | 1690 | 44 | 0.66 | -6.5 |
| 61 | 60 | 5 | 487 | 17 | 0.77 | -12.8 |
| 64 | 70 | 16 | 1338 | 17 | 0.81 | -13.1 |
| 67 | 46 | 5 | 706 | 30 | 0.63 | -13.4 |
| 68 | 47 | 5 | 653 | 37 | 0.61 | -13.4 |

FIG. 24

FIELD-BASED SIMILARITY SEARCH SYSTEM AND METHOD

CROSS REFERENCE TO RELATED APPLICATIONS

The present application is a Divisional application of U.S. patent application Ser. No. 12/544,889 filed on Aug. 20, 2009, now U.S. Pat. No. 8,014,990 which was a Divisional application of U.S. patent application Ser. No. 10/102,902 filed on Mar. 22, 2002, now abandoned which claims the benefit of Provisional Application No. 60/278,260 which was filed on Mar. 23, 2001 by Blake Fitch, et al., assigned to International Business Machines Corporation, and which are incorporated herein by reference.

This Application is related to U.S. Pat. No. 6,349,265 assigned to International Business Machines Corporation, and U.S. patent application Ser. No. 09/275,568 filed on Mar. 24, 1999 (assigned to International Business Machines Corporation), which are also incorporated herein by reference.

BACKGROUND OF THE INVENTION

1. Field of the Invention

The present invention generally relates to a field-based similarity search system and method, and more particularly, a field-based similarity search system and method which identifies similar molecules based on fragment pair feature similarities.

2. Description of the Related Art

An important problem in drug discovery efforts is finding molecules that have a similar function to a molecule known to be active towards a biological target or that elicits a biological response of interest. Commonly, such detailed structural information of the mechanism of action is unknown. Although, there exist several conventional methods to search for or create such compounds, the most common involves a conjectured conformation of the molecule of interest (e.g., query molecule), or the repeated application of a method to a series of query conformers.

More specifically, there exist several conventional methods of aligning a group of flexible molecules to a particular query conformation (e.g., molecular superposition) using computer-assisted drug design (see, e.g., C. Lemmen, T. Lengauer, and G. Klebe, FLEXS: A method for fast flexible ligand superposition. *Journal of Medicinal Chemistry*, 41:4502-4520, 1998; Michael D. Miller, Robert P. Sheridan, and Simon K. Kearsley, Sq: A program for rapidly producing pharmacophorically relevent molecular superpositions, *J. Med. Chem.*, 42:1505-1514, 1999; Christian Lemmen, Claus Hiller, and Thomas Lengauer, Rigfit: a new approach to superimposing ligand molecules. *Journal of Computer-Aided Molecular Design*, 11:357 368, 1997; Gerhard Klebe, Thomas Mietzner, and Frank Weber, Different approaches toward an automatic structural alignment of drug molecules: Applications to sterol mimics, thrombin and thermolysin inhibitors, *Journal of Computer-Aided Molecular Design*, 8:751778, 1994; Simon K. Kearsley and Graham M. Smith, An alternative method for the alignment of molecular structures: maximizing electrostatic and steric overlap, *Journal of Computer Aided Molecular Design*, 8:565 582, 1994; Colin McMartin and Regine S. Bohacek, Flexible matching of test ligands to a 3d pharmacophore using a molecular superposition force field: Comparison of predicted and experimental conformations of inhibitors of three enzymes. *J. Med. Chem.*, 42:1505 1514, 1999; S. Handschuh, M. Wagener, and J. Gasteiger, Superposition of three-dimensional chemical structures allowing for conformational flexibility by a hybrid method, *J. Chem. Inf. Comput. Sci.*, 38:220-232, 1998; J. Mestres. D. C. Rohrer, and G. M. Maggiora, A molecular field-based similarity approach to pharmacophoric pattern recognition, *J. Mol. Graph. Modeling*, 15:114-21, 1997; Y. C. Martin, M. G. Bures, E. A. Danaher, J. DeLazzer, J. Lico, and P. A. Pavlik, A fast new approach to pharmacophore mapping and its application to dopaminergic and benzodiazepine agonists, *Journal of Computer Aided Molecular Design*, 7:83-102, 1993; Peter Willett, Searching for pharmacophoric patterns in databases of three dimensional chemical structures, *Journal of Molecular Recognition*, 8:290-303, 1995; Gareth Jones, Peter Willett, and Robin C. Glen, A genetic algorithm for flexible molecular overlay and pharmacophore elucidation, *J. Comput.-Aided Mol. Des.*, 9:532-549, 1995; D. A. Thorner, D. J. Wild, P. Willett, and P. M. Wright, Similarity searching in files of three-dimensional chemical structures: flexible field-based searching of molecular electrostatic potentials, *Journal of Chemical Information and Computer Sciences*, 36:900 908, 1996; D. J. Wild and P. Willett. Similarity searching in files of 3-dimensional chemical structures—alignment of molecular electrostatic potential fields with a genetic algorithm, *Journal of Chemical Information and Computer Sciences*, 36:159-167, 1996; David A. Thorner, Peter Willett, Robert C. Glen, P. M. Wright, and Robin Taylor, Similarity searching in files of three-dimensional chemical structures" representation and searching of molecular electrostatic potentials using field-graphs, *J. Comput.-Aided Mol. Des.*, 1:163 174, 1997; and Gerhard Klebe, Structural alignment of molecules, In Hugo Kubinyi, editor, *3D QSAR in Drug Design, pages* 173-199. ESCOM, Leiden, 1993).

In the absence of structural information regarding the ligand receptor or ligand-enzyme complex, structural alignment is a way of both elucidating important features responsible for activity (Ki Hwan Kim, List of comfa references 1993-1997, In Hugo Kubinyi, Gerd Folkers, and Yvonne C. Martin, editors, *3D QSAR in Drug Design*, volume 3, pages 317 338, Kluwer, Dordrecht/Boston/London, 1998; and Gerhard Klebe, Comparative molecular similarity indicies analysis, In Hugo Kubinyi, Gerd Folkers, and Yvonne C. Martin, editors, *3D QSAR in Drug Design*, volume 3, pages 87-104, Kluwer, Dordrecht/Boston/London, 1998) and a means of finding new molecules with similar or better activity (Michael D. Miller, Robert P. Sheridan, and Simon K. Kearsley, Sq: A program for rapidly producing pharmacophorically relevent molecular superpositions, *J. Med. Chem.*, 42:1505-1514, 1999; Andrew C. Good and Jonathan S. Mason, Three dimensional structure database searches, In Kenny B. Lipkowitz and Donald B. Boyd, editors, *Reviews in Computational Chemistry*, volume 7, chapter 2, pages 67 117. VCH Publishers, Inc., New York, 1996; and Peter Willett, Searching for pharmacophoric patterns in databases of three dimensional chemical structures, *Journal of Molecular Recognition*, 8:290-303, 1995).

Generally, when one is attempting to elucidate spatial and chemical information about the nature of the host ligand interaction, one often begins with the alignment of a series of active compounds based on some kind of alignment rule. Unfortunately, this process is riddled with difficulties and assumptions about the relevant conformations, relevant features, importance of internal strain, the role of hydrogen bonds, electrostatics, solvation and hydrophobicity, as well as more profound concerns such as whether compounds in a data set even bind at the receptor site via the same mechanism. It is clear that no single method for alignment will settle these issues across widely varying contexts.

Several conventional superposition methods reported are field-based (see, e.g., Michael D. Miller, Robert P. Sheridan, and Simon K. Kearsley, Sq: A program for rapidly producing pharmacophorically relevent molecular superpositions, *J. Med. Chem.*, 42:1505-1514, 1999; Christian Lemmen, Claus Hiller, and Thomas Lengauer, Rigfit: a new approach to superimposing ligand molecules, *Journal of Computer-Aided Molecular Design*, 11:357 368, 1997; J. Mestres. D. C. Rohrer, and G. M. Maggiora, A molecular field-based similarity approach to pharmacophoric pattern recognition, *J. Mol. Graph. Modeling*, 15:114-21 1997; and D. A. Thorner, D. J. Wild, P. Willett, and P. M. Wright, Similarity searching in files of three-dimensional chemical structures: flexible field-based searching of molecular electrostatic potentials, *Journal of Chemical Information and Computer Sciences*, 36:900 908, 1996). An attractive aspect of field-based approaches is the potential for incorporating high levels of theory into the field. Apart from the difficulties and expense of deploying high level quantum mechanical calculations, the design of a system that can utilize the results of such calculations for use in similarity analysis is considered forward looking.

However, such conventional field-based approaches are confined to a particular field definition. For example, a conventional system designed for simplistic, phenomenological fields, is not available for fields derived from quantum mechanical calculations. This severely limits the versatility of these conventional systems.

SUMMARY OF THE INVENTION

In view of the foregoing, and other problems, disadvantages, and drawbacks of conventional systems and methods, the present invention has been devised having as its objective, to provide a fast and efficient field-based similarity search system and method.

The present invention includes a field-based similarity search system which includes a database for storing at least one candidate molecule, an input device for inputting a query molecule, and a processor for identifying a candidate molecule which is similar to the query molecule based on a similarity of fragment pair features.

Specifically, the processor may identify a feature of a query molecule fragment pair. The processor may also match a query molecule fragment pair feature with a candidate molecule fragment pair feature, and retrieve a candidate molecule fragment pair having at least a predetermined number of matching features.

Further, the processor may align retrieved fragment pairs using a pose clustering method. The processor may also construct a fully aligned candidate molecule by assembling retrieved fragment pairs. The processor may also generate the fragment pair for the query molecule.

In addition, the inventive system may include a display device for displaying an output from the processor. The system may also include a memory device for storing a query molecule fragment pair feature. Further, the memory device may store data and instructions to be executed by the processor.

More specifically, the fragment pair may include two neighboring fragments connected by a rotatable bond at a specific dihedral angle. Further, the feature may include a generalization of a CoMMA descriptor.

In another aspect, the present invention includes an inventive field-based similarity search method which includes generating a conformational space representation and an arbitrary description of a three-dimensional property field for a flexible molecule, characterizing parts of the flexible molecule and representing a query molecule using the arbitrary description for a comparison with the conformational space representation, and aligning the parts to the query molecule and assembling the parts to form an alignment onto the query molecule.

Alternatively, the inventive field-based similarity search method may include identifying a feature of a query molecule fragment pair, matching a query molecule fragment pair feature with a candidate molecule fragment pair feature; and retrieving a candidate molecule fragment pair having at least a predetermined number of matching features.

Alternatively, the inventive field-based similarity search method may include a method for finding alignments of a flexible molecule to a query molecule. The method may include, representing a conformation space of the flexible molecule, generating an arbitrary description of a three-dimensional property field of the flexible molecule, characterizing parts of the flexible molecule using the arbitrary description, representing a query molecule using the arbitrary description for a comparison with molecules represented by the conformation space, aligning the parts of the flexible molecule to the query molecule, and assembling the parts of the flexible molecule to form an alignment thereof onto the query molecule.

In another aspect, the present invention includes a programmable storage medium tangibly embodying a program of machine-readable instructions executable by a digital processing apparatus to perform a similarity search method, the method including generating a conformational space representation and an arbitrary description of a three-dimensional property field for a flexible molecule, characterizing parts of the flexible molecule and representing a query molecule using the arbitrary description for a comparison with the conformational space representation, and aligning the parts to the query molecule and assembling the parts to form an alignment onto the query molecule.

With its unique and novel features, the present invention provides a fast and efficient field-based similarity search system and method which are not confined to a particular field definition. For example, the inventive system and method may be designed for simplistic, phenomenological fields, as well as for fields derived from quantum mechanical calculations. Therefore, the claimed system and method provides improved versatility over conventional systems and methods.

BRIEF DESCRIPTION OF THE DRAWINGS

The foregoing and other objects, aspects and advantages will be better understood from the following detailed description of a preferred embodiment of the invention with reference to the drawings, in which:

FIG. 3 illustrates a schematic representation of a fragment graph;

FIG. 4 illustrates Table I which provides the signs of axes which may be chosen to fix a sensing according to the present invention;

FIG. 7(A) illustrates a dihydrofolate molecule and FIG. 7(B) illustrates a methotrexate molecule;

FIG. 8 illustrates Table III which shows experimental parameters used by the inventors;

FIG. 10 illustrates Table IV which has cells corresponding to rectangular bins from which the discriminant space is partitioned, according to the present invention;

FIG. 12 illustrates Table V which shows the distribution of the correspondence cluster sizes for rigid body superposition of the crystal structure of methotrexate onto that of dihydrofolate;

FIG. 13 illustrates Table VI which shows the statistics for the fragment and fragment pair partitioning of methotrexate;

FIG. 14 illustrates Table VIII which shows the distribution of the correspondence cluster sizes for flexible superposition of methotrexate onto the crystal structure of dihydrofolate;

FIG. 15 illustrates the number of bases that survive each assembly phase for the flexible superposition of methotrexate onto the crystal structure of dihydrofolate;

FIG. 19 illustrates Table IX which shows the fragmentation statistics on the additional molecules added to the database, in the inventors' experiments;

FIG. 21 illustrates Table X which shows each molecule's distribution of correspondence cluster sizes for fragment pair alignments;

FIG. 22 illustrates Table XI which shows the distribution of cluster sizes for the DHFR inhibitors;

FIG. 23 illustrates Table XII which shows the alignment and assembly timings, top Carbo scores, and total number of candidates for each ligand investigated;

FIG. 24 illustrates Table XIII which shows the alignment and assembly timings, top Carbo scores, and total number of candidates for the eight DHFR inhibitors investigated;

DETAILED DESCRIPTION OF EXEMPLARY EMBODIMENTS OF THE INVENTION

Figure 1:
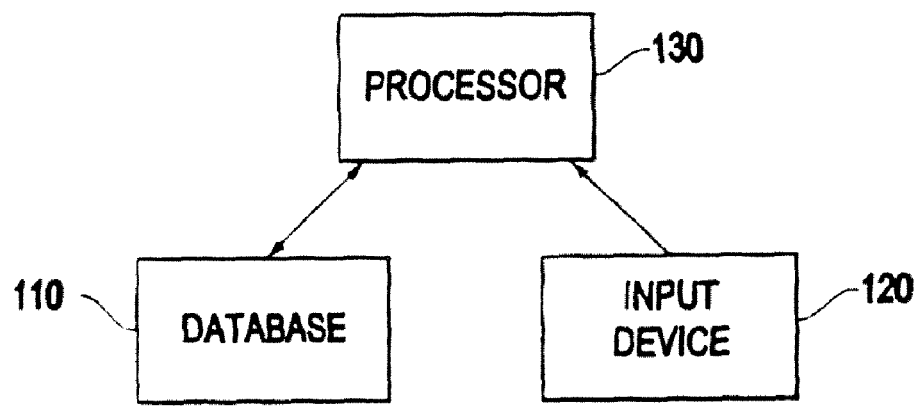
FIG. 1 illustrates a schematic diagram of an inventive field-based similarity search system 100 according to the present invention.

Referring now to the drawings, FIG. 1 illustrates an inventive system 100 for field-based similarity searching (e.g., three dimensional searching) databases (e.g., flexible molecule databases).

As shown in FIG. 1, the inventive field-based similarity search system 100 includes a database 110 for storing at least one candidate molecule (e.g., a plurality of candidate molecules), an input device 120 (e.g., a keyboard or mouse) for inputting a query molecule, and a processor 130 (e.g., microprocessor) for identifying a candidate molecule which is similar to said query molecule based on a similarity of fragment pair features.

Specifically, the processor 130 may be a central processing unit (CPU) or a plurality of processors. Further, the processor 130 may identify a feature of a query molecule fragment pair. The processor 130 may also match a query molecule fragment pair feature with a candidate molecule fragment pair feature, and retrieve a candidate molecule fragment pair having at least a predetermined number of matching features. Further, the inventive system 100 may also include a memory device (e.g., RAM, ROM, etc.) for storing instructions for performing an operation using the processor 130. The memory device may also be used to store features, fragment pairs, matches of molecules, or any other data used or generated by the inventive system.

Further, inventive system 100 may also store specific algorithms in the memory device for performing a particular operation. The processor 130 may, therefore, access the memory device and/or database in order to process data according to a particular algorithm stored therein. For instance, the processor 130 may access data stored in the memory device or database (e.g., plurality of databases) which pertains to a query molecule or candidate molecule, in order to process such data and, therefore, determine is the candidate molecule is similar to the query molecule.

Further, the processor 130 may align retrieved fragment pairs using a pose clustering method. The processor 130 may also construct a fully aligned candidate molecule by assembling retrieved fragment pairs. The processor may also generate the fragment pair for the query molecule.

Further, the inventive system 100 may include a display device (e.g., video display unit) for displaying, for example, the query molecule, a candidate molecule, or other data used or generated by the inventive system 100. Further, a user may utilize the display device in order to help the user direct an operation in the inventive system 100. For instance, the display device may be used with the input device 120 so that the user may input instructions, data, etc. into the inventive system for storage in the database or memory device, and/or for processing by the processor 130.

An important feature of the inventive system 100 is that it allows the incorporation of context-specific information to balance considerations in a manner suitable to the problem at hand. The result is that one-time calibrations of similarity measures are inappropriate. Therefore, the basis of a similarity search is tunable to the particular context being considered.

In short, the present invention provides a systematic way of treating field-based similarity searching, without being confined to a particular field definition. In other words, the present invention allows for fields ranging from simplistic, phenomenological fields, like the examples discussed below, to fields derived from quantum mechanical calculations.

Overview

The inventive system 100 includes a database 110 which may include, for example, a set of molecules over which to conduct a search. This set of molecules may be an explicitly defined set of molecules, or may be a "virtual" set of molecules (e.g., a set which is built from all or some combination of smaller molecules according to specified rules.

For example, the database 110 may include a database of molecules, each with a single conformation, which is defined by a specification of its atoms, bonds and atomic positions. Atom specification may be by element, a chemical tag denoting an atom in a certain environment, and/or an atom that is to be treated in a certain way. Bond specification may involve a reference to two atoms, and a bond type. Bond types can be a valance bond order, a chemical tag denoting the bond in a particular environment, and/or a bond that is to be treated in a certain way.

For a single conformation of the molecule to be specified, Cartesian coordinates may be assigned to each atom. The co-ordinates can originate from x-ray crystal structure, nuclear magnetic resonance (NMR) solution structure, molecular mechanics, molecular dynamics, any form of quantum mechanical or hybrid quantum/classical calculations, or an entirely heuristical procedure.

Further, additional rules regarding how the molecules could combine to make larger molecules may be added. For example, given two molecules A and B, a rule may specify that A and B can combine to make C by a series of operations, such as alignment of atoms of A and B, addition or deletion of atoms and/or bonds in A and/or B, and conformation adjustments to A, B, and/or C. In this case, the database 110 would include all or some of the possible C's that result from the application of a rule set comprised of any of the operations mentioned above.

Specifically, the inventive system 100 represents the conformational space for each molecule by a set of rules, rather than being explicitly defined. This eliminates the intractable storage requirements that explicit enumeration requires for large sets of flexible molecules.

Specifically, each molecule may be partitioned into smaller fragments by the selection (either manual or algorithmic) of a set of bonds to cleave. The allowed angles for a cleavage bond is enumerated explicitly for each pair of conformers in the corresponding node sets. Conformers of the fragments isolated by cleavage bonds, however, are explicitly enumerated. A data representation in the form of a graph is constructed such that each node of this graph is a set of fragment conformers and each edge of this graph is constructed such that each node of conformer of the molecule can then be expressed as a selection of one member in each node set (fragment conformer) and edge set (cleavage bond angle).

Alternatively, the fragment sets of molecules may be left disconnected in terms of a graph describing a larger molecule. A set of rules, likened to reaction descriptions, embodied as transformations such as adding or deleting atoms and/or bonds, and/or translating and/or rotating positions, can then be expressed in terms of matching topology of a fragment, and thus need not refer to particular fragment sets, but any fragment set possessing one or more instances of the topology on which the transformations operate. The rules may then denote the resulting conformations of their application. The result of any such application can itself by included in the pool of available fragment sets for further application.

A key to the system 100 is that it avoids the need to search every conformation of every molecule and apply a similarity metric to the query at each possible alignment. This is done by using selected features from fragment pairs to align them to the query. Thus, unlike previous works (e.g., see U.S. Pat. No. 6,349,265 and U.S. Prov. patent application Ser. No. 09/275, 568) the inventive system 100 uses fragment pairs in place of the stored molecule. With said technology, features from the fragment pairs in the database may be matched with features of the query molecule.

Once features have been matched, the transformations used to align them may be classified by said methodology. The transformations may be grouped together, for example, using a clustering procedure or a binning procedure. A score may be assigned to the transformation groups based on group membership and/or other criteria based on the chemical and/ or conformational similarity of the implied fragment pair alignment. Based on this scoring criteria, one may select the best alignments of fragment pairs to the query.

The user, therefore, has the option of combining the fragment pairs that have been aligned to the query to create larger or complete molecules. For example, a user may be restricted to only suggesting molecules in a given database. In this case, combining rules ensure that fragment pairs are not combined with others that do not share a common fragment conformation. If partial structures are allowed, then after combinations of fragment pairs are made, each product may be evaluated by applying scoring criteria that qualifies candidates. Otherwise, candidate qualification criteria may be applied only to completely constructed structures.

Alternatively, combinations of fragments according to reaction rules as described above may be allowed. These fragments need not belong to the same molecule. Combinations of fragment pairs may be directed by reaction rules, rather than the restriction of a common conformation. Each time a combination is made, the result may be checked for candidate qualification. Candidates may be stored, for example, in a database. The resulting set of molecule conformers may also be ranked according to a similarity metric.

Flexible Molecules

The inventive system 100 may represent the conformational space of a flexible molecule in terms of fragments and torsional angles of allowed conformations. A user definable property field may be used to compute features of fragment pairs. Features may be considered generalizations of CoMMA descriptors that characterize local regions of the property field by its local moments (B. D. Silverman and D. E. Platt, Comparative molecular moment analysis (comma): 3d-qsar without molecular superposition, *J. Med. Chem.*, 39:2129 2140, 1996). The features are invariant under coordinate system transformations.

Features taken from a query molecule are used to form alignments with fragment pairs in the database. An assembly algorithm may then be used to merge the fragment pairs into full structures, aligned to the query. Important to the system 100 is the use of a context adaptive descriptor scaling procedure as the basis for similarity. This helps to allow the user to tune the weights of the various feature components based on examples relevant to the particular context under investigation.

The property fields may range from simple, phenomenological fields, to fields derived from quantum mechanical calculations. For instance, the inventors have applied the inventive system 100 to a dihydrofolate/methotrexate benchmark system, to show that when one injects relevant contextual information into the descriptor scaling procedure, better results are obtained more efficiently.

Thus, the inventors have shown how the inventive system 100 provides for an effective and efficient search. For instance, the inventors have provided computer times for a query from a database that represents approximately 23 million conformers of nine flexible molecules.

Conformational Space and Quantum Mechanical Calculations

Generally, the conformational space for drug-like molecules can become quite appreciable. Some conventional methods represent the conformational space of a molecule as a collection of rigid fragments with preselected torsions (Gerhard Klebe and Thomas Mietzner, A fast and efficient method for generating biologically relevant conformations, *Journal of Computer Aided Molecular Design*, 8:583-606, 1994). Other approaches prepare a database of representative conformations (Simon K. Kearsley, Dennis J. Underwood, Robert P. Sheridan, and Michael D. Miller, Flexibases: A way to enhance the use of molecular docking methods, *Journal of Computer Aided Molecular Design*, 8:565 582, 1994; Mathew Hahn, Three-dimensional shape-based searching of conformationally flexible molecules, *J. Chem. Comput. Sci.*, 37:80-86, 1996), or compute conformations on the fly (Gareth Jones, Peter Willett, and Robin C. Glen, A genetic algorithm for flexible molecular overlay and pharmacophore elucidation, *J. Comput.-Aided Mol. Des.*, 9:532-549, 1995).

The inventive system 100, on the other hand, is based on fragmenting molecules into more manageable partitions. In particular, the inventive system 100 chooses as a smallest irreducible unit of characterization as the fragment pair rather than the fragment. This treatment makes conformational space more manageable than conventional forms of treatment.

Setting out to address flexible superposition via potentially sophisticated property fields, one must give special attention to reducing the number of similarity evaluations that are to be performed, while maintaining some degree of confidence that the space has been covered. The inventive system 100 attempts to pre-process as much as possible, while still leaving enough tunability to adapt to the context of the investigation. The system 100 seeks a practical tradeoff of the size of conformational space, and the need for fragment pairs as large as possible to maximize the relevance of the computer property fields.

More specifically, the inventive system 100 decomposes the conformational space of molecules to fragments. Then, to minimize boundary effects, the system 100 computes the property field on pairs of fragments. From the computer property fields of the fragment pairs, several features may be sampled and stored.

As noted briefly above, features may be considered to be generalizations of CoMMA descriptors that characterize local regions of the property field by its local moments. They are invariant under coordinate system transformations. To query the database for molecules that are similar to a particular molecule (e.g., the query molecule) features are calculated for the query molecule, and fragment pairs that contain a sufficient number of similar features are retrieved.

An important point is that, due to the coordinate system invariance of the features, the retrieval can happen without any alignment, or optimization over rotational and translational degrees of freedom. The alignment of retrieved fragment pairs on the query may be determined by a pose clustering procedure from the individual feature correspondences. Finally, to construct full aligned candidate molecules, the retrieved fragment pairs may be assembled by an incremental buildup procedure, similar in principle to ones used in docking (Matthias Rarey, Berud Kramer, Thomas Lengauer, and Gerhard Klebe, A fast flexible docking method using an incremental construction algorithm, *J. Mol. Biol.*, 261:470 489, 1996)) and de novo design (Hans J. Bohm, The computer program ludi: A new method for the de novo design of enzyme inhibitors, *J. Comput.-Aided. Mol. Des.*, 6:6178, 1992).

Fragment Pairs

There are two types of complexity in a database of three dimensional molecular structures: first, the conformational variety of individual molecules, and second, in the case of a virtual combinatorial library, the combinatorial variety that results from the possibility of synthesizing a large number of different molecules from a small number of reagents. Generally, the total number of three-dimensional structures grows exponentially both with the number of rotatable bonds and the number or reagents. Therefore, such a database should be efficiently represented and stored.

A molecule can be partitioned into a fragment graph. This is an acyclic graph that consists of fragment nodes connected by rotatable bond edges. Within a fragment node, there may be one zero, one or several rotatable bonds, as well as other degrees of freedom such as ring conformations. Given a molecule, there are in general multiple possible ways of partitioning it into a fragment graph. Typically, a fragment node may consist of about 10 heavy atoms, for example an aromatic ring plus some substituents.

Figure 2:
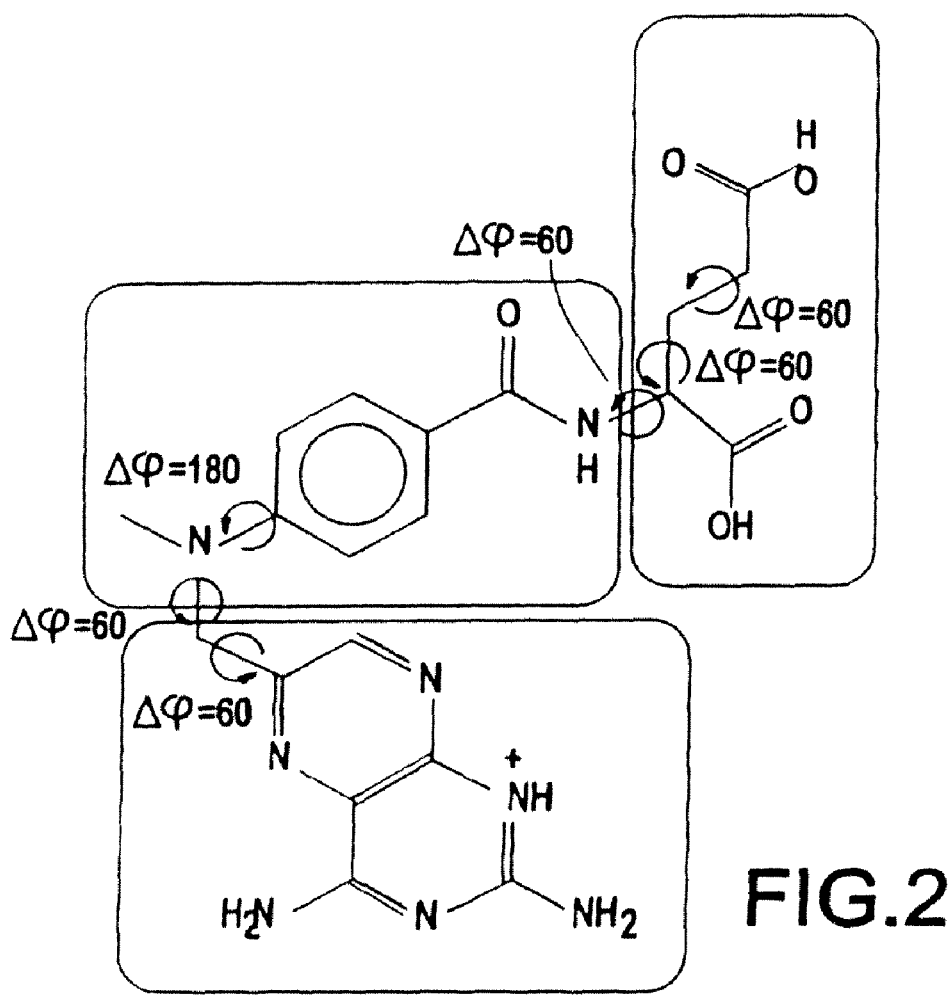
FIG. 2 illustrates a fragmentation and conformational expansion of methotrexate.

FIG. 2 shows a sample partition. Specifically, FIG. 2 shows fragmentation and conformational expansion of methotrexate. As shown here, single bonds may be sampled with a resolution of $\Delta\phi=60°$, the aniline bond with $\Delta\phi=180°$. Further, the molecule in FIG. 2 is partitioned into three fragments.

Further, the substructure represented by a fragment node can in general assume several different conformations. A specific conformation of a fragment node may be referred to as a fragment. A fragment pair consists of two neighboring fragments connected by a rotatable bond at a specific dihedral angle. A schematic representation of a fragment graph is depicted in FIG. 3.

Fragment pairs are important entities in the inventive system 100. Property fields are defined and calculated on fragment pairs, and the similarity search is based on rotationally invariant features that are calculated from those property fields. The assumption that underlies the use of fragment pairs is that a property field calculated in the interior of an isolated fragment pair is a good local approximation of the property field of the composite molecule.

Conceptually, the use of fragment pairs may be considered as equivalent to using overlapping fragments, with the overlap being about half their size. This has advantages both for the recognition and for the assembly steps. First, the fragmentation locally distorts the property field in those places where the molecule is cut. By using fragment pairs, the regions around the fragment joints are always in the interior of at least one fragment pair, such that meaningful local descriptors can be calculated for them. Further, an aligned database molecule is constructed by assembling fragment pairs that have one fragment in common, and which both locally match the query with compatible orientations. Thus, the relevant dihedral range of the connecting rotatable bonds determined (e.g. from steric and energetic criteria) is already available in the pre-computed fragment pairs.

Obviously, this approach is suitable both for conventional molecule libraries, as well as for virtual libraries supporting combinatorial chemistry approaches. The efficiency of the fragment pair representation is best discussed by way of an example. As indicated in FIG. 2, the conformational space of methorexate is spanned essentially by six rotatable bonds. If five of the bonds are sampled in steps of 60°, and one bond is sampled at 180°, the total number of conformations is $$C_{MOL} = 6^5 \cdot 2 = 15552. \tag{1}$$

In practice, fewer conformations have to be considered because some are sterically forbidden. Similar to equation (1), $C_{FP1}$, the number of fragment pairs from the lower and middle fragment node, and $C_{FP2}$, the number of fragment pairs from the middle and upper fragment node are $$C_{FP1} = 6 \cdot 6 \cdot 2 = 72, \; C_{FP2} = 2 \cdot 6 \cdot 36 = 432. \tag{2}$$

The total number of fragment pairs is therefore 72+432=504. Furthermore, the size of a fragment pair is in this example only about ⅔ of the size of the whole molecule, with a corresponding smaller number of local descriptors, so that the fragment pair representation needs about 50 times less storage than the brute force enumeration.

More generally, for a molecule consisting of n fragments, each of which has $C_{FRAG}$ conformations, and which are connected by rotational bond edges that are sampled in $C_{RBE}$ steps, the total number of conformation is $$C_{MOL} = C_{FRAG}^M \cdot C_{RBE}^{n-1}, \tag{3}$$

where n−1 is the number of rotatable bond edges. In comparison, the total number of fragment pairs is $$C_{FP} = (n-1) \cdot C_{FRAG}^2 \cdot C_{RBE}. \tag{4}$$

Note that equation (3) grows exponentially with n, whereas equation (4) only depends linearly on n.

The Property Field

A basis for the three dimensional similarity searching and alignment are two property fields $\mu(\vec{r})$ and $\rho(\vec{r})$. The inventive system 100 makes no assumptions about these fields, except that $\mu(\vec{r})$ is scalar and positive. It may also be assumed that $\rho(\vec{r})$ is a single scalar, but this can be straightforwardly extended to multiple scalars, vectors or tensors.

Both fields $\mu(\vec{r})$ and $\rho(\vec{r})$ are used to identify similar regions in query and database molecules. Their geometrical alignment however, is performed solely on the basis of field $\mu(\vec{r})$.

A simple-minded property field can be defined as:

$$\mu(\vec{r}) = \frac{1}{(\sqrt{2\pi\sigma})^3} \sum_{j=1}^{N_{atoms}} A_j \exp \frac{-(\vec{r}-\vec{a}_j)^2}{2\sigma^2} \tag{5}$$

$$\rho(\vec{r}) = \mu(\vec{r}) - \bar{\mu}.$$

Here the j-th atom is located $\alpha_j$, and its electronegativity, $A_j$ is given according to the Allred scale (Bodie E. Douglas, Darl H. McDaniel, and John Alexander, *Concepts and Models of Inorganic Chemistry*. John Wiley & Sons, 1983). The inventors used the following values: $A_C$=2.6, $A_O$=3.4, $A_N$=3.0, $A_H$=2.2, $A_P$=2.2, $A_F$=4.0. $\sigma$ is a parameter that controls the range of the Gaussian smearing function. In their work, the inventors used $\sigma$=0.5 Å. The rationale is to choose a value as big as possible, but small enough for the property field not to be too uniform and unspecific. $\bar{\mu}$ is the average of $\mu(\vec{r})$ over all space. $\mu(\vec{r})$ is positive and $\rho(\vec{r})$ is analogous to a neutral charge distribution.

Another possible choice of a property field is $$\mu(\vec{r}) = \frac{1}{(\sqrt{2\pi\sigma})^3} \sum_{j=1}^{N_{atoms}} M_j \exp \frac{-(\vec{r}-\vec{a}_j)^2}{2\sigma^2} \tag{6}$$

$$\rho(\vec{r}) = \frac{1}{(\sqrt{2\pi\sigma})^3} \sum_{j=1}^{N_{atoms}} Q_j \exp \frac{-(\vec{r}-\vec{a}_j)^2}{2\sigma^2}$$

where $M_j$ is the atomic mass and $Q_j$ is the atomic charge computed by considering the "fraction of ionic character" of each bond in the molecule (M. Karplus and R. N. Porter, *Atoms and Molecules*, W. A. Benjamin, Inc., Menlo Park, Calif., 1971).

These example fields are by no means intended to offer new insight into processes that underlie the chemistry of the present invention. To exemplify and prototype the inventive system 100, the inventors selected the property field defined by equation (5) because of its simplicity. In spite of its simplicity, however, when this property field is used, the inventive system 100 performs adequately, and thus may serve in the future as a base level, against which more elaborate fields may be benchmarked.

Obviously, the choice of the property fields will have a great effect both on the selectivity and on the efficiency of the search. The point is that the preferred choice depends on the application and on the questions asked. The exploration of different alternative fields is intended to be part of the process of adapting the inventive system 100 to a certain domain.

Possible fields are by no means restricted to "smeared out" atomic properties. The present invention may be intended to make use of fields derived from quantum mechanical calculations.

Descriptors and Feature Generation

Given the property fields $\mu(\vec{r})$ and $\rho(\vec{r})$, the inventive system 100 may construct a set of local, rotationally invariant, moment-based descriptors. If the property fields of the query molecule and a database fragment pair are similar, these descriptors will have similar values. Since the descriptors are rotationally variant, no alignment is necessary, and the comparison can be performed very quickly.

The similarity of the descriptors alone is an important but not a sufficient criterion for the similarity of the fields. However, together with the descriptors the inventive system 100 stores information on their relative positions and orientations within the query and database structures. When a database structure has enough descriptors similar to the query, the relative positions and orientations of the descriptors are compared. If these are also consistent, the two structures may be considered similar, and an approximate alignment is deduced from this information.

Note that in order to obtain the alignment, no explicit (and costly) optimization of a property field overlap function with respect to translation and rotation operators needs to be performed in the inventive system 100. However, if desired, such an optimization can afterwards be applied to a small set of promising candidates, starting from near-optimal initial conditions.

The first step in the construction of the descriptors is the partitioning of the volume occupied by the structure into overlapping scoops. If the property fields are defined by smearing out atomic properties $A_j$, (as in the two examples set forth above), this may be performed as follows: Let $\{\vec{s}_k\}$ be a set of points within or around the structure, such that the spheres with radius R around these points provide a highly overlapping covering of the relevant regions of the property fields.

Each of these spheres is called a "scoop". Further, define a ramping function $$\Delta(a) = \begin{cases} 1 & a \le R \\ 0 - a/R & a > R \end{cases} \tag{7}$$

and a window function $$h(r) = \begin{cases} 1 & r \le R \\ 0 & r > R \end{cases} \tag{8}$$

Therefore, the "attenuated atomic properties" that contribute to the k-th scoop may, therefore, be given by $$A_j^{(k)} = \Delta(|\vec{a}_j - \vec{s}_k|) \cdot A_j \tag{9}$$

and the k-th scoop's property field is $$\mu_k(\vec{r}) = h(|\vec{r} - \vec{s}_k|) \cdot \frac{1}{(\sqrt{2\pi}\sigma)^3} \sum_j^{N_{atoms}} A_j^{(k)} \exp\frac{-(\vec{r} - \vec{a}_j)^2}{2\sigma^2} \tag{10}$$

and corresponding for $\rho_k(\vec{r})$, as in equation (5). The intention of the ramping function (7) is that the property fields $\mu_k$ and $\rho_k$ (and therefore the descriptors) are continuous functions of the location of the scoop center $\vec{s}_k$.

For general property fields $\mu(\vec{r})$ and $\rho(\vec{r})$ that are not obtained by smearing out atomic properties, scoop property fields can simply be obtained by setting $$\mu_k(\vec{r}) = h(|\vec{r} - \vec{s}_k|) \cdot \mu(\vec{r}), \tag{11}$$

and correspondingly for $\rho(\vec{r})$.

For example, the set of points $\{\vec{s}_k\}$ may be the set of all atom positions, and R=3 Å. With this, the scoops may objects of intermediate size, larger than a functional group, but smaller than a fragment pair. Typically, a scoop may contain 6 to 8 non-hydrogen atoms.

Having defined a set of scoops and their associated local property fields $\mu_k$ and $\rho_k$, rotationally invariant descriptors may be constructed. There will be a descriptor consisting of 16 real numbers for each scoop. To simplify the notation, in the following, the index k that numbers the scoops was dropped, and the continuum fields was replaced by the discretized versions $\mu_i$ and $\rho_i$ defined on a grid of points $\{\vec{r}_i | i = 1, \ldots, N\}$. For the grid, a face-centered cubic lattice (other types of lattices can also be used) of unit cell length $\Delta R = R/18$ within each scoop of radius R has been used. Further, the grid spacing $\Delta R$ has been determined by varying the grid orientation with respect to the atoms in the scoop, and making sure that the resulting descriptors, as described below, do not significantly depend on the orientation.

The zeroth moments of the fields are $$M = \sum_{i=1}^{N} \mu_i, \quad Q = \sum_{i=1}^{N} \rho_i \tag{12}$$

In the case of the property field defined by equation (6), M and Q correspond to total mass and total charge within the scoop.

The center of the $\mu$-field is defined by $$\vec{c}_\mu = \frac{1}{M} \sum_{i=1}^{N} \mu_i \vec{r}_i \tag{13}$$

and the center of the $\rho$ field by $$\vec{c}_\rho = \begin{cases} \frac{1}{Q}\vec{b} & \text{if } |Q| > \varepsilon_Q \\ \frac{1}{3b^2}\left(B\vec{b} - \frac{\vec{b}^t B \vec{b}}{4b^2}\vec{b}\right) & \text{otherwise} \end{cases} \tag{14}$$

where $\vec{b}$ and B are dipole and quadrupole moment of the $\rho$-field with respect to the origin of the laboratory coordinate system, $$\vec{b} = \sum_{i=1}^{N} \rho_i \vec{r}_i \quad B = \sum_{i=1}^{N} \rho_i (3\vec{r}_i \vec{r}_i^t - r_i^2 \mathbb{1}) \tag{15}$$

and the superscript t stands for transposition. In the case of the property field defined by equation (6), $\vec{C}_\mu$ is the center of mass, and the first line of equation (14) is the center of charge. The center of charge may be defined only if the scoop has a net charge (e.g. if the charge is larger than the threshold $\varepsilon_Q$. Otherwise, the second line of equation (14) calculates the center of dipole.

The inertial tensor J and a cubic vector $\vec{j}$ with respect to $\vec{C}_\mu$, the center of are defined as $$J = \sum_{i=1}^{N} \mu_i (r_i'^2 \mathbb{1} - \vec{r}_i' \vec{r}_i'^t) \tag{16}$$

$$\vec{j} = \sum_{i=1}^{N} \mu_i r_i'^2 \vec{r}_i' \tag{17}$$

where $\vec{r}_i' = \vec{r}_i - \vec{C}_\mu$. Similarly, dipole moment $\vec{p}$ and quadrupole moment Q of the $\rho$-field with respect to $\vec{C}_\rho$, the center of $\rho$, may be defined as follows:

$$\vec{p} = \sum_{i=1}^{N} \rho_i \vec{r}_i'' \quad (18)$$

$$Q = \sum_{i=1}^{N} \rho_i (3\vec{r}_i'' \vec{r}_i''^t - r_i''^2 \mathbb{1}) \quad (19)$$

where $\vec{r}_i'' = \vec{r}_i - \vec{C}_\rho$.

It is important to note that the quantities (e.g., equations) (17)-(19) are expressed in a uniquely defined scoop-internal coordinate system so that they no longer depend on the arbitrary choice of the laboratory frame. Therefore, the descriptors of different scoops can be compared without prior alignment. The axes of the scoop internal coordinate system are given by the eigenvectors of the inertial tensor J:

$$J\vec{v}_n = J_n \vec{v}_n, n=1, 2, 3. \quad (20)$$

The positive numbers $J_n$ are the inertial moments. The vectors $\vec{v}_n$ can be arranged into the columns of an orthonormal matrix V. An arbitrary vector may be then transformed from the laboratory frame to the internal frame by left-multiplying it with $V^t$.

In order to uniquely define the internal coordinate system, (i) the ordering, and (ii) the sensing (i.e. the signs) of the coordinate axes should be fixed.

The ordering is defined by $J_1 \leq J_2 \leq J_3$. If two or three of the eigenvalues of J are degenerate, then there are no unique eigenvectors, but rather two- or three-dimensional eigenspaces, there is no well-defined inertial coordinate system, and the corresponding scoop is not used to generate a descriptor. Degeneracy in this context means that two eigenvalues are equal to within some threshold that may depend on the choice of property field. The degeneracy condition is $$J_2/J_1 < 1+\epsilon_J \text{ or } J_3/J_2 < 1+\epsilon_J. \quad (21)$$

To fix the sensing, the dimensionless asymmetry vector was defined by $$\vec{\alpha} = \begin{pmatrix} RJ_1 & 0 & 0 \\ 0 & RJ_2 & 0 \\ 0 & 0 & RJ_3 \end{pmatrix}^{-1} V^t \vec{j} \quad (22)$$

where $\vec{j}$ is the cubic vector from equation (17), and the signs of the axes were selected according to Table I illustrated in FIG. 4.

The sign $s \in \{-1, 1\}$ is determined by requiring right-handedness, i.e. det V=1. The table above represents a unique choice of the axes sensing depending only on the cubic vector $\vec{j}$.

If two, or three components of $\alpha$ are within some chosen threshold of zero, one is left with two or even four different equally admissible choices for the axes sensing. For descriptors stored in the database, an arbitrary choice may simply be taken. For the query features that are to be matched against the database, a descriptor is generated for each admissible choice of axes sensing. For the present data, the inventors used the duplication condition $\alpha_n/RJ_n < 0.02$.

Figures 5, 6:
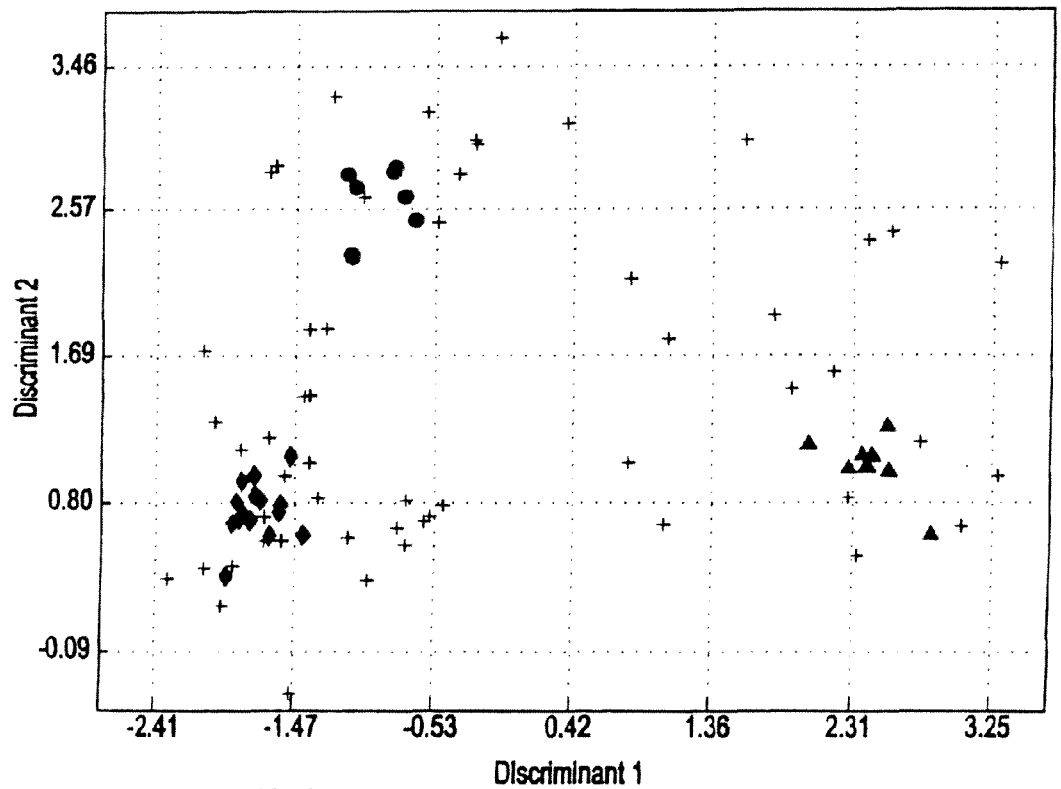
FIG. 5 illustrates Table II which shows the number of components which may be present in an sample descriptor.
FIG. 6 illustrates a graph showing the distribution of features after mapping into a 2-dimensional space by way of discriminant analysis.

As a result, the CoMMA descriptor $X_k$ for the k-th scoop, which may be called a feature, may consist of the d=16 real numbers which are shown in Table II in FIG. 5.

If the $\rho$ field is more complex than a scalar field (e.g., a combination of several scalars) or a vector or a tensor field, then the first and second moments $\vec{p}$ and Q will have a correspondingly greater number of components, and d, the number of components of the descriptor $X_k$ is larger than 16.

Since the vector and tensor quantities in the descriptor are expressed in the internal coordinate system, which only depends on local properties of the molecule, the descriptor is completely independent of the laboratory frame. This has two important implications: first, two scoop descriptors can be compared against each other without prior alignment, and second, if two descriptors are found to be similar, the two corresponding molecules can be locally aligned by simply overlaying the internal coordinate systems of the two scoops.

Descriptor Scaling and Quantization

The scoop descriptors $X_k = (X_{k1}, \ldots, X_{kd})$ cannot be used straightforwardly to define similarity between scoops because the components $X_{k1}, X_{k2}, \ldots$ have different physical units, and because the different components may be more or less important for the similarity search at hand. For example, it may be important in a particular application of this method to recognize and distinguish between some specific set of structural motifs or chemical functional groups in identifying fragment pairs from a database to align on a query molecule. In a different application of the inventive system 100, it may be more important instead to recognize and distinguish a different set of motifs, or regions of electrical polarity. Clearly, a useful system should be able to adapt to what is meaningful to the user in assessing similarity.

The inventors, therefore, defined a distance measure that weights the different descriptors according to their importance as perceived from a training set of descriptors. The training data consists of a number of sample descriptors that are categorized into groups. From this, the inventive system 100 may "learn" two types of descriptor variations: Important variations may be considered those that occur systematically between descriptors from different groups. Such variations may be used to define the distance measure. The descriptors within a group are considered similar, and the distance measure is made to ignore these types of variations.

While there is a vast repertoire of methods from the disciplines of classification and pattern recognition to address this task, the inventive system 100 may simply use Fisher's linear discriminant analysis. It provides a linear mapping from the d-dimensional descriptor space into a lower-dimensional space:

$$Y_k = W^t X^k \quad (23)$$

where W is a d×p matrix with $p \leq d$.

The discriminant matrix W is calculated from the user-supplied classification of a sample of descriptors $X_k$, into p+1 groups. The within-group scatter matrix $S_w$ is the average covariance matrix of descriptors that are in the same group, and the between-group scatter matrix $S_b$ is the covariance of the group centroids (Richard O. Duda and Peter E. Hart, *Pattern Classification and Scene Analysis*, John Wiley & Sons, Inc., New York, 1973). The discriminant matrix W is defined through the maximization of the criterion function:

$$J(W) = \frac{|W^t S_b W|}{|W^t S_w W|}. \quad (24)$$

This optimization criterion selects W such that the distances between the $Y_k$ within the same group are minimized, whereas the distances between the groups' centroids are maximized. Numerically, W may be calculated using a generalized eigenvalue routine (IBM, Poughkeepsie, N.Y. *Engineering and Scientific Subroutine Library for AIX, Version* 3, Guide and Reference, 1997).

To allow for a fast database lookup of stored descriptors that are similar to a query, descriptor space may be quantized. Descriptors that fall within the same compartment may be considered similar, and are matched. Those that fall into different compartments do not match.

For example, the compartments may be defined by a rectilinear grid in discriminant space (i.e. in the space of the $Y_k$). The grid spacings $s_j$ are chosen such that a grid cell can accommodate the typical scatter within a group. This is done by a heuristic that sets the bin width $s_j$ to four times the largest standard deviation of the j-th component (j=1, ..., p) within an individual group, and the right end of the leftmost bin to the minimum over all groups.

For example, FIG. 6 illustrates a sample distribution of features in discriminant space. Specifically, FIG. 6 shows the distribution of features after mapping into a 2-D space by way of discriminant analysis, with the functional grouping. The features marked with diamonds, triangles and circles represent the three groups. The remaining features are marked with plus symbols. The query is represented by 53 features, and a single conformation of the database molecule (the crystallographic one) is represented by 56 features.

Although the scaling and quantization in the inventive system 100 may be fairly simple, it is robust. Moreover, the inventive system 100 does accomplish a context-adapted descriptor calibration and similarity measure, utilizing a user-defined training set of descriptors. Missed matches as a consequence of cell boundaries are not as likely in the low dimension in which the grid is defined as they would be for higher-dimensional situations. Since there is redundancy in the set of scoops characterizing a molecule, a meaningful alignment will be recovered if just a fraction of them are actually matched.

A virtue of linear mappings (e.g., equation (23)), in comparison to, for example, neural networks, is that linear mappings have a limited number of parameters and require only a relatively small training set, which is important for practical applications. Furthermore, the mapping (e.g., equation (23)) and the subsequent discretization are exactly invariant under overall linear transformations of the descriptors. This means that the calibration and quantization scheme does not depend on whether, for example, length is measured in meters or Angstroms, and mass in grams or amu.

The training set may be chosen according to the following criteria: the different groups should be selected to contain examples of structural or functional units that are relevant for the similarity search. Within the individual groups, members should represent the kinds of variations that occur in the descriptor database, like experimental uncertainty in bond lengths and angles, different environments of functional groups, and different conformations deemed irrelevant for the problem at hand.

The Feature Database

The previous section generated a context-adapted mapping from descriptor space to an integer set of feature keys. These keys are simply the indices that label the cells in discriminant space. The use of a hash table and fast integer key lookup methods supports efficient queries against large databases, with access times largely independent of database size.

In principle, compared to a method that would use a detailed, fully continuous distance metric, the quantization of the descriptors to produce the keys causes a loss of sensitivity (more false negatives), and a loss of selectivity (more false positives) in the similarity search. However, the set of descriptors that describe a molecule may be highly redundant, so that an incomplete set of scoop matches still leads to a complete alignment of the molecules. Furthermore, false positive matches are reduced in a subsequent clustering step since false positive matches do not occur consistently.

The feature database may be the product of two inputs: a set of descriptors, generated from all conformations of a selection of fragment graphs, and the context-adapted descriptor-to-key mapping. The feature database is a hash table, whose keys are given by evaluating the mapping on the descriptors. An entry in the hash table consists of a reference back to a fragment pair, and a description of the internal frame associated with the descriptor. The explicit values of the descriptors are not stored in the feature database. The thrifty use of memory by the feature database is important for the scalability of the inventive system 100.

Generally, the calculation of the descriptor set for all the fragment pairs of the fragment graphs may be an expensive part of the inventive system 100. However, the descriptor set may be computed only one time, in a preprocessing step, and then the set may be stored. Application of the descriptor to key mapping is fairly cheap and quick. As the domain context is varied, the descriptor-to-key mapping will change, and different feature databases can be created to query against. Finally, a given feature database can be queried very rapidly from the keys of query features, with any number of queries, including differing conformations of the same molecule, as well as differing molecules.

Feature Correspondence

The feature database may be used to align fragment pairs to the query molecule. The basic idea is to calculate scoops, descriptors, and keys for the query in the same way as for the fragment pairs stored in the database. Each query key then accesses the matching entries in the feature database. Each pair of query and database scoops that have the same key may be referred to as a correspondence.

By overlaying the internal coordinate axes of such a scoop pair, each correspondence implies a certain alignment of a stored fragment pair onto the query. Whereas such a single correspondence might be coincidental, a significant alignment—what may be referred to as a hypothesis—is inferred when several independent correspondences from different regions of the query and fragment pair support the same relative orientation of the two. This assumption is a basis of pose-clustering methods (G. Stockman, Object recognition and localization via pose clustering, *Computer Vision, Graphics, and Image Processing*, 40:361387, 1987). A selected number of the strongest hypotheses may be passed on to the assembly.

The feature correspondence process may, therefore, include construction of all correspondences by keyed access from the query to the feature database, clustering of the correspondences, and construction of the hypotheses as average alignments of the significant clusters.

The internal coordinate system that is associated with a feature may be specified by its origin $\vec{c}_\mu$, and an orthonormal system of inertial eigenvectors V (e.g., see equations (13) and (20)). The transformation of laboratory frame coordinates $\vec{x}$ into internal coordinates may be given by $$T: \vec{x} \mapsto V^t(\vec{x} - \vec{c}_\mu). \tag{25}$$

Given a correspondence between a query feature $X_q$ and a stored feature $X_s$, and the two associated transformations $T_q$ and $T_s$, the transformation that aligns the stored fragment pair coordinates onto the query is $$T_{qs} = T^{-1}{}_q \circ T_s : \vec{x} \mapsto \vec{c}_{\mu,q} + V_q V_s^{-1}(\vec{x} - \vec{c}_{\mu,s}). \quad (26)$$

This is a putative alignment of the fragment pair represented in the database onto the query molecule, based on a single feature correspondence.

However, it would be impractical and prohibitively expensive to evaluate and score each such alignment separately. In the inventive system 100, therefore, the set of all putative alignments may be divided into clusters. In order to perform clustering, a metric in the space of transformations (e.g., see equation (26)) may be required. For example, the inventors have used the following metric:

$$d(T_{qs}, T_{q's'}) = |T_{qs}(\vec{x}_0) - T_{q's'}(\vec{x}_0)| + 2\alpha \tan\left(\frac{1}{2} d_{rot}\right) \quad (27)$$

$$d_{rot} = a\cos\left(\frac{1}{2}(Tr\{V_{q'} V_{s'}^t V_s V_q^t\} - 1)\right) \quad (28)$$

if s and s' are from the same fragment pair, and $d(T_{qs}, T_{q's'}) = \infty$ if they are from different fragment pairs. $\vec{x}_0$ is the center of geometry of the fragment pair coordinates, and the first term on the right hand side of equation (27) is simply the Euclidean distance between the transformed fragment pair centers. $V_{q'} V_s^t V_s V_q^t$ is the rotation part of the transformation $T_{q's'} \circ T^{-1}_{qs}$ that maps a set of coordinates transformed by $T_{qs}$ onto the one transformed by $T_{q's'}$, and $d_{rot}$ is the magnitude of the angle of that rotation.

Further, the function $f(x)=2 \tan N/2$ is close to the identity for small angles, but becomes large when x goes towards $\pi$. This function may be used to make sure that transformations with very different rotations are considered very far apart. The parameter $\alpha$ provides a measure of the relative weighting of orientation and translation for the transformation distance. For example, $\alpha=3$ Å may be selected for all fragment pairs.

Having defined a metric, the clustering may be performed. For example, the hierarchical clustering method GO3ECF implemented in the NAG library (NAG Ltd., Oxford, UK. *The NAG Fortran Library Manual*, Mark 16, 1993), with the complete-linkage distance updating method, may be used. Hierarchical clustering may be selected over partitional, because the latter is cumbersome for non-Euclidean metrics like equation (27), and the complete-linkage method because it produces the most compact clusters, which is desirable for the subsequent averaging (Anil K. Jain and Richard C. Dubes, *Algorithm for Clustering Data*, Prentice Hall, 1988).

The only parameter of the clustering step may be the distance level $d_{clust}$ at which the dendrogram is cut. For instance, after some investigation (e.g., the choice for $d_{clust}$ used in the present work was made based on a number of experiments with the DHF-MTX system. However, results were relatively insensitive to values in the range of 2.5 to 4.0 Å. This value is probably appropriate for studies using the same clustering algorithm, transformation distance metric, with fragments that are approximately 10 heavy atoms in size, and for nuclear placement of scoops) the inventors have used $d_{clust}=3$ Å. Note that if $d_{clust}$ is too large, what should be distinct clusters will be merged and the average transformation will not be representative of any transformation of these distinct clusters. On the other hand, if $d_{clust}$ is too small, the number of members in each cluster is small and no clusters emerge with sufficient signal.

For hypothesis building, the largest and therefore most significant clusters may be selected, and average transformations calculated. For instance, consider a cluster of n transformations $T_1, \ldots T_n$, each one represented by $$T_i : \vec{x} \mapsto \vec{t}_i + R_i \vec{x}, \quad i=1, \ldots, n. \quad (29)$$

Representations given by equations (29) and (26) are related by $R = V_q V_s^t$ and $\vec{t} = \vec{c}_{\mu,q} - R\vec{c}_{\mu,s}$. The average rotation may be calculated as $$R_{av} = UW, \quad (30)$$

$$\text{where } UDW = \sum_{i=1}^{N} R_i$$

is a singular value decomposition (SVD) of $\Sigma_i R_i$ (W. Dan Curtis, Adam L. Janin, and Karel Zikan, A note on averaging rotations, In *IEEE Virtual Reality Annual International Symposium*, pages 377-385, IEEE, 1993).

This is well-defined as long as the rotations in the cluster are not too different. In the situation where rotations vary widely, the notion itself of an average rotation becomes disputable. The average translation vector $\vec{t}_{av}$ is calculated by requiring that the fragment pair center $\vec{x}_0$ under the average transformation is the arithmetic average of the fragment pair center under the individual transformations in the cluster, $$\vec{t}_{av} = \frac{1}{2}\left[\sum_{i=1}^{n} \vec{t}_i + R_i \vec{x}_0\right] - R_{av} \vec{x}_0. \quad (31)$$

The average transformation for the cluster may be therefore $T : \vec{x} \mapsto \vec{t}_{av} + R_{av} \vec{x}$. For example, all feature correspondences may carry an equal weight both in the clustering and averaging steps. Alternatively, it may be considered that some correspondences are more significant than others.

Summing up, for each query feature, the descriptor-to-key mapping may form a correspondence with all stored features that have the same key value. The set of all such pairs may be clustered according to the metric in transformation space. There might be correspondences involving many different stored fragment pairs, but the correspondences within one cluster may only refer to the same fragment pair.

Further, the largest clusters, according to a user-defined minimum cluster size $n_{clust}$ may be selected. For each cluster, the average transformation may be calculated and applied to the coordinate of the fragment pair from whose features it was derived. The result is a set of hypotheses, that is, fragment pairs aligned on the query.

Assembly

The assembly process in the inventive system 100 may begin with this set of hypotheses: fragment pairs positioned in the query frame according to the transformations derived in the clustering procedure. These fragment pairs may belong to any molecule in the database. An objective is to merge these fragment pairs into complete, aligned structures. The assembly algorithm should be able to process as much in parallel as possible.

If only fragment pairs belonging to the same fragment graph are allowed to be merged, the structures that result from the assembly process will be conformers of those molecules that were used to build the database. However, if fragment pairs from different fragment graphs are allowed to merge, new structures may be created through the assembly. Furthermore, pieces of larger structures may qualify as matches to the query.

The assembly may be an iterative process, where each iteration step begins with a set of fragment pairs and/or partially assembled structures, and produces a set of partially or fully assembled structures that have increased in size by one fragment. Whereas the overall iteration loop runs sequentially, within a step, many fragment pairs or partial structures can be processed in parallel.

At the beginning of each step, fragment pairs and any partial structures from previous steps may be grouped together and referred to as bases. In other words, a base may be a group of adjacent fragments, that have been aligned to the query, and connected with specific torsional angles of the rotatable bonds. All atom coordinates may be expressed in the query frame. In addition, a base carries a record of which fragment nodes it contains, and which fragment pairs could be used to grow it.

The first phase of an assembly step may be termed the base expansion phase. In this phase, the list of potential merges of fragment pairs with bases may be determined. It results from consideration of the fronts of the growing bases. The front of a base is defined as the set of rotatable bond edges between a matched and an unmatched fragment node on the fragment graph. Any fragment pair from the set of hypotheses that includes both a frontal rotatable bond edge and matches the fragment conformer present in the base can potentially merge with the base. A merge between a base and fragment pair may occur if the root mean square distance computed between corresponding atoms in the fragments that are common to the base and the fragment pair is less than a threshold. Note that during the assembly process a hypothesis fragment pair can be used for merges many times, onto multiple growing bases.

There are different ways to merge a base and a fragment pair that have close, but not identical atom positions of the common fragment. First, one could leave the base fixed and superpose the fragment pair onto the base's fragment. In the other extreme, one could leave the fragment pair fixed and superpose the base onto the fragment in the fragment pair.

However, the inventors have used an intermediate option, which is constructed by joining the base and the fragment pair, and then determining the least squares alignment (K. S. Arun, T. S. Huang, and S. D. Blostein, Least square fitting of two 3-d point sets, *IEEE Transactions on Pattern Analysis and Machine Intelligence*, PAMI-9(5):698 700, 1987) of the unique corresponding atoms in the original base and the grown one, and in the fragment pair and the grown base. The atoms of the common fragment are not necessarily included in this calculation. Note, that due to the merging, the orientation and position of a base depends not only on the fragment pairs that went into it, but also on the order in which they were merged. Therefore, multiple identical bases can be produced with slightly different positions and orientations relative to the query molecule.

After each merge, a bump check may be performed, which checks whether atoms from the newly added fragment are too close to those that were in the base before. For instance, the inventors have used a threshold of 1.7 Å A non-bonded atom-atom distance (e.g., the value of 1.7 Å chosen for the bump check parameters used in this work is rather small. Therefore, some high energy conformations are used as fragment pairs and also some high energy candidates are produced during assembly. The value was chosen to screen out only the worst cases of steric overlap in order to assess the method with a larger work load. The performance of the method improves if this parameter is increased).

After a bump check, a shape screen may be applied, which prevents the base from growing too far outside the query's volume. The screen may be performed simply by verifying that no atom in the base is more than a threshold distance from the closest atom in the query. For instance, this threshold may default to 3.5 Å.

Bases that pass the shape screen may be then scored against the query. For example, the default scoring function may be a simple Carbo function, as used in other work (R. Carbo, L. Leyda, and M. Amaua, How similar is a molecule to another? An electron density measure of similarity between two molecular structures, *Int. J. Quant. Chem.*, 17:1185, 1189, 1980).

$$Q = \frac{1}{N_q} \int_{R^3} \left( \sum_{j=1}^{N_q} h(\vec{x} - \vec{a}_j) \right) \left( \sum_{j=1}^{N_b} h(\vec{x} - \vec{b}_j) \right) d^3\vec{x}, \tag{32}$$

where $\vec{a}_j$ is the atom coordinate of the $j^{th}$ query atom, $\vec{b}_j$ is the atom coordinate of the $j^{th}$ atom in the base, and $h(\vec{x}) = \pi^{-3/4} \tau^{-3/2} \exp(-x^2/2\tau^2)$ is a normalized three dimensional Gaussian density with $\tau=1$ Å. $N_a$ and $N_b$ are the numbers of atoms in the query molecule and the base, respectively. Scoring functions can vary widely in their sophistication (Andrew C. Good and W. Graham Richards, Explicit calculation of 3d molecular similarity, In Hugo Kubinyi, Gerd Folkers, and Yvonne C. Martin, editors, *3D QSAR in Drug Design*, volume 2, pages 321-338, Kluwer Academic Publishers, Great Britain, 1996). The inventors have chosen equation (32) for its simplicity.

A base that passes certain criteria may qualify as a candidate, meaning that it may be considered a successful match to the query. For instance, a base may be considered a candidate if it has some minimum number of fragments, passes all applicable checks and/or has a sufficient score with respect to the scoring function in use.

Bases that have no opportunities for growth may be removed from consideration in subsequent iterations of the assembly process. The bases remaining may be used as input to the next iteration of the assembly phase. The assembly process may be terminated when there are no bases left for consideration (e.g., when there are no bases left to grow).

Note that the procedure may be considered exhaustive in that all candidate alignments may be produced if they qualify with respect to the bump check, shape screen and scoring criteria. The inventive system 100 may, therefore, attempt to produce the better candidates early. For example, in their application of the inventive system 100 discussed below, the inventors produced all possible qualifying candidate alignments that could be constructed from the aligned fragment pairs submitted to the assembly phase.

EXAMPLE

Application of the Present Invention to Dihydrofolate and Methotrexate

For example, the inventors have applied the inventive system 100 to the case of dihydrofolate (DHF) and methotrexate (MTX). This case has been the subject of study for numerous methods of superposition (Michael D. Miller, Robert P. Sheridan, and Simon K. Kearsley, Sq: A program for rapidly producing pharmacophorically relevent molecular superpositions, *J. Med. Chem.*, 42:1505-1514, 1999; Christian Lemmen and Thomas Lengauer, Time-efficient flexible superposition of medium-sized molecules, *Journal of Computer-Aided Molecular Design*, 11:357 368, 1997; Simon K. Kearsley and Graham M. Smith, An alternative method for the alignment of molecular structures: maximizing electrostatic and steric overlap, *Journal of Computer Aided Molecular Design*, 8:565 582, 1994) as well as docking (Matthias Rarey, Berud Kramer, Thomas Lengauer, and Gerhard Klebe, A fast flexible docking method using an incremental construction algorithm, *J. Mol. Biol.*, 261:470 489, 1996; David M. Lorber and Brian K. Shoichet, Flexible ligand docking using conformational ensembles, *Protein Science*, 7:938 950, 1998). In fact, the case has become a benchmark for such methods, as it exhibits an interesting aspect that the most reasonable superposition from the perspective of topology is different from the superposition that can be deduced from aligning the enzyme parts of the crystal structures of ligand-enzyme complexes of DHF and MTX bound to dihydrofolate reductase (DHFR) (Gerhard Klebe. Structural alignment of molecules, In Hugo Kubinyi, editor, *3D QSAR in Drug Design*, pages 173-199, ESCOM, Leiden, 1993).

The latter superposition can be understood in terms of electrostatics and hydrogen bonding sites (Hugo Kubinyi, Similarity and dissimilarity: A medicinal chemist's view, In Hugo Kubinyi, Gerd Folkers, and Yvonne C. Martin, editors, *3D QSAR in Drug Design*, volume 3, pages 317-338. Kluwer, Dordrecht/Boston/London, 1998). The MTX-DHF system may thus serve as a probe to characterize how such methods weight the importance of topological similarity, electrostatic similarity, and potential non-bonded interactions. The inventors chose this case as their case study to characterize how the inventive system 100 performs, using the very simply property field detailed above.

To this end, the inventors described two experiments, which illustrate the importance of feature classification. The first considers the alignment of a rigid conformation of MTX on a rigid conformation of DHF. Both conformations are extracted from the crystal structures of the molecules bound to DHFR. Features are computed at atom centers and grouped according to a classification scheme derived with knowledge of the respective binding modes observed in the crystal structures. This functional-based grouping (e.g., as shown in FIGS. 7(A) and 7(B)) is compared to the case where all features are classified equally, and every query feature is compared to every stored feature.

For example, FIGS. 7(A) and 7(B) show the definition of the three groups for the descriptor scaling. The first group may consist of the descriptors derived from scoops around the guanidine of the pteridine system. There are four such scoops for DHF, and four for MTX. Therefore, the first group consists of 8 descriptors. Similarly, the second group is made up of 8 descriptors from the chain linking the pteridine and benzamide rings, and the third group of 16 descriptors from around the p-amino-benzamide ring.

Taking DHF as the query, MTX may be aligned, for example, under the two conditions of classification, and the results compared. It should be noted that knowledge of the particular binding mode is not a requirement for application of the inventive system 100. If, however, one has such information, one should be able to use it to better characterize the meaning of similarity in a similarity search.

As a second experiment the inventors used DHF as a query molecule on a database that represents the full conformational space of MTX. The features were classified using two schemes. The first scheme is the functional-based grouping described above. The second scheme assumes no knowledge of the binding modes and simply groups features by the element type (e.g., C, N, or O) of the central atom.

Comparison of the results of using these two schemes illustrates the value of injecting relevant context into the feature classification scheme. The inventors compared the workload consequent from these two feature classification schemes, and concluded with the top scoring alignments assembled from the fragment pairs of MTX. As noted below, reasonable results are obtained with both grouping schemes. However, when features are classified with the functional-based (i.e., context-derived) scheme, the results are obtained more efficiently and are of higher quality, as assessed by the Carbo scoring function or by visual inspection.

Rigid Body Superposition

Structures of DHF and MTX were extracted from the crystal structures with PDB identifiers 1dhf and 4dfr respectively. 1dhf provides the coordinates of DHF bound to the human form of the enzyme DHFR(N. J. Prendergast, T. J. DeCamp, P. L. Smith, and J. H. Fresheim, Expression and site-directed mutagenesis of human dihydrogolate reductase, *Biochemistry*, 27:3664, 1988). 4dfr provides the coordinates of MTX bound to an *E. coli* strain (J. T. Bolin, D. J. Filman, D. A. Matthew, R. C. Hamlin, and J. Kraut, Structures of *escherichia coli* and *lactobacillus casei* dihydrogolate reductase refined at 1.7 angstroms resolution. i. general features and binding of methotrexate, *J. Biol. Chem.*, 257:13650, 1982) of DHFR. No attempts were made to optimize the structures with quantum or classical methods. Thus, the ring distortion and out-of-plane bending as observed in the crystal structures were left intact. Hydrogen atoms were added using Cerius2 (Program Cerius2, distributed by Molecular Simulations Inc., 9685 Scranton Rd. San Diego Calif. 92121-3752).

Features were computed according to the parameters in Table III, as shown in FIG. 8. Placing scoops at atomic nuclei produced 53 scoops for DHF and 56 for MTX. Further, feature groups were defined using the functional-based classification scheme illustrated in FIGS. 7(A) and 7(B). These group definitions are somewhat similar to those defined in a QSAR study of DHFR inhibitors by Hopfinger (William J. III Dunn, Anton J. Hopfinger, Cornel Cantana, and Chaya Duraiswami, Solution of the conformation and alignment tensors for the binding of trimethoprim and its analog to dihydrofolate reductase: 3d quantitative structure-activity relationship study using molecular shape analysis, 3-way partial least squares, and a 3-way factor analysis, *J. Med. Chem.*, 39:4825 4832, 1996). The definitions emphasize regions of the molecule important for binding and avoid features from parts of the structures that appear unessential for activity.

Figure 9:
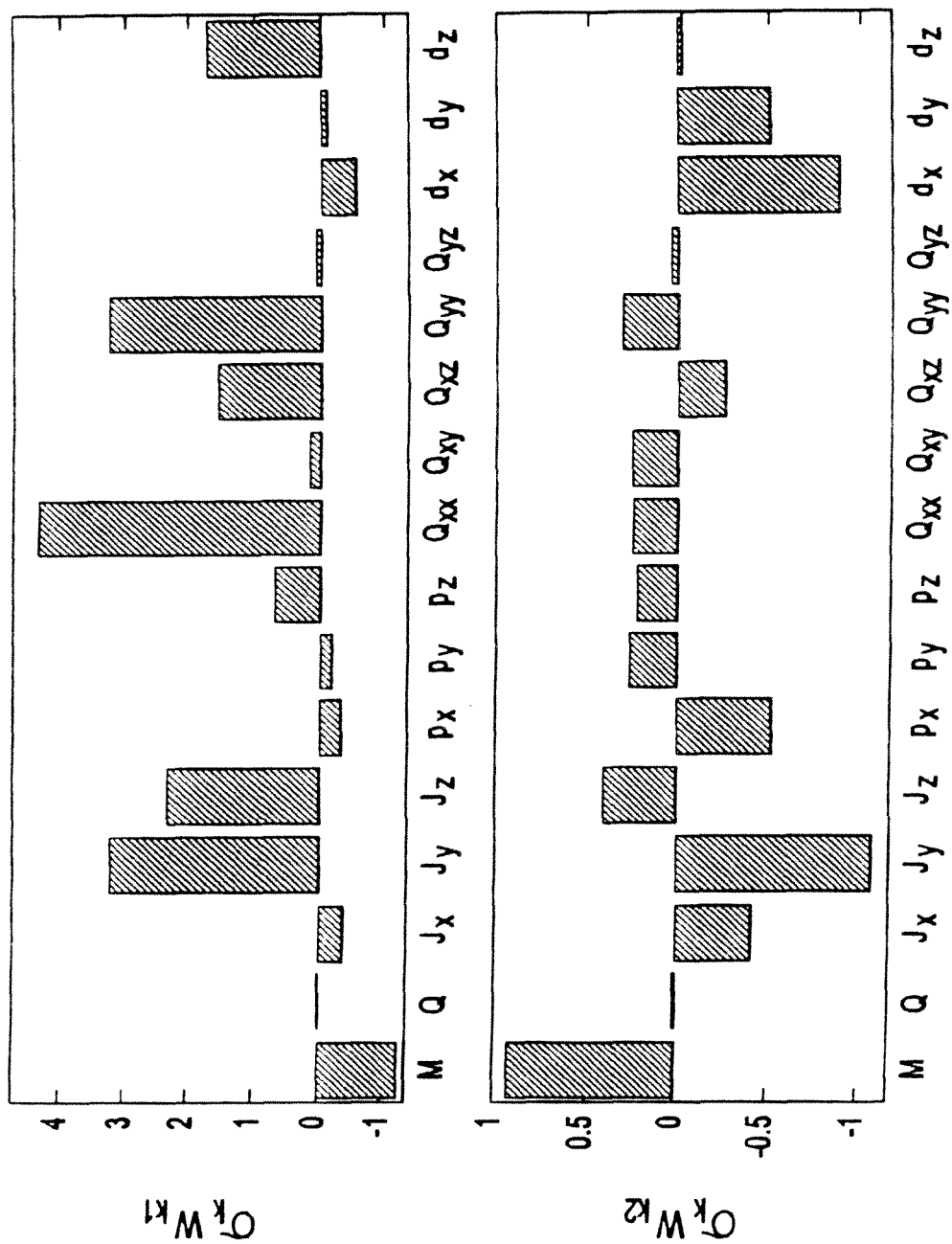
FIG. 9 illustrates a Fisher discriminant matrix.

The loadings of the two Fisher discriminants derived from the functional grouping are shown in FIG. 9 (e.g., the Fisher discriminant matrix W (see, e.g., equation (23))). As shown in FIG. 9, W represents the linear mapping from the 16-dimensional local scoop descriptors (as described above) to the 2-dimensional discriminant space in which the similarity measure is defined. In order to make the components $W_{kj}$ comparable, they have been multiplied by the standard deviation $\sigma_k$ of the k-th descriptor (k=1, . . . , 16), sampled over the total pool of features.

Further, the first discriminant has domain loadings in $Q_{xx}$ and $Q_{yy}$, as well as the inertial $J_y$ and $J_z$ components of the feature. Large Q components with the present property field arise when the differences in electronegativity with respect to the average lie further from their center of dipole. The second discriminant is most sensitive to M, the integral of the electronegativity property field over the scoop, and differences in $J_z$ from $J_x$ to $J_y$, which may be seen as a crude measure of planarity of field within the scoop. Differing training sets will lead to a different feature weighting in discriminant space.

The atom-centered features of both DHF and MTX, once projected onto the Fisher discriminants resulting from the functional grouping, are partitioned into bins. The size of the bins in each dimension is set to four times the standard deviation of the largest group.

Figure 11B:
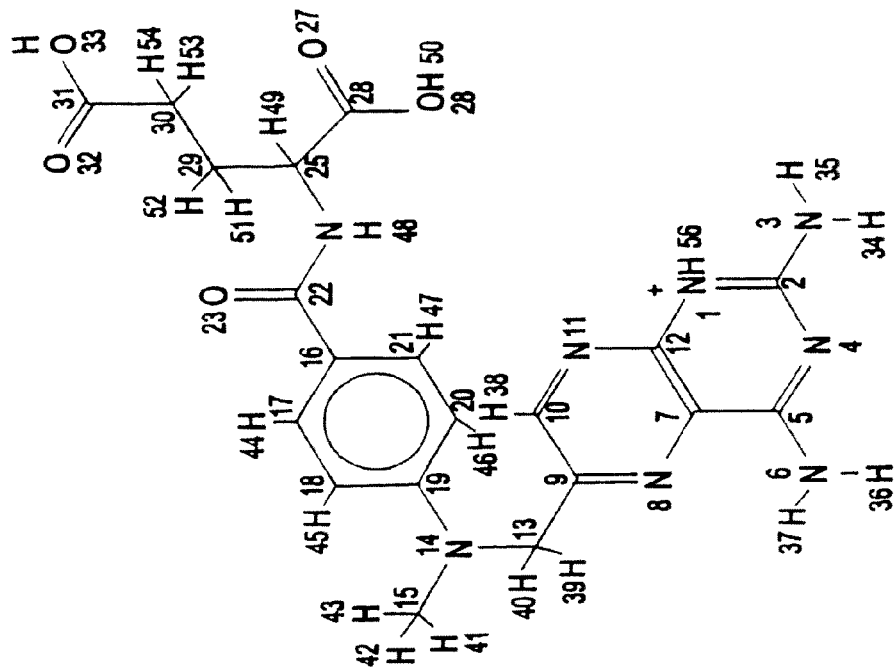
FIG. 11(B) illustrates a methotrexate molecule having the features labeled by the name of the central atom of the corresponding scoop.
Figure 11A:
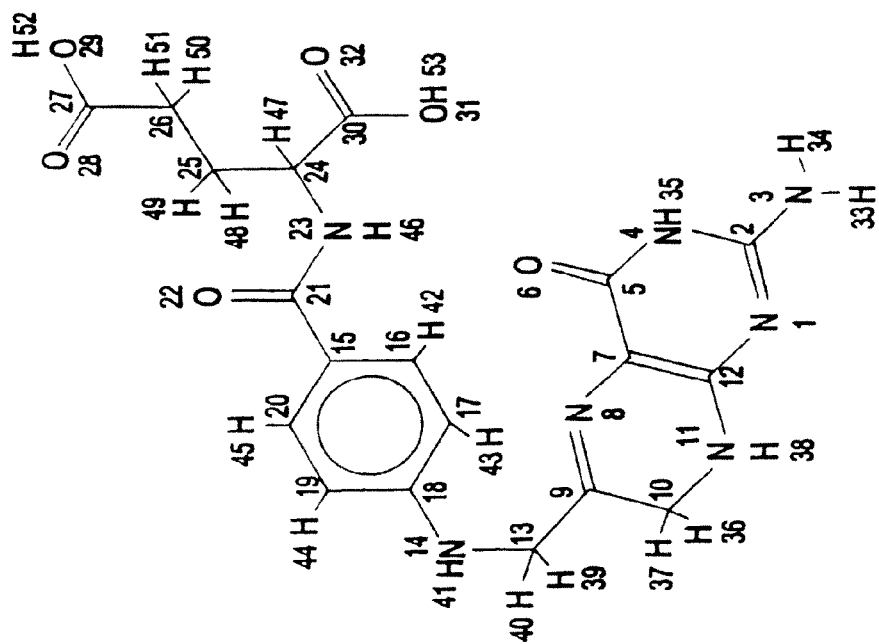
FIG. 11(A) illustrates a dihydrofolate molecule having the features labeled by the name of the central atom of the corresponding scoop.

The resulting partitioning scheme is shown in FIG. 6 and Table IV in FIG. 10. As shown in Table IV, to define similarity, the discriminant space depicted in FIG. 6 is partitioned into rectangular bins. Each bin corresponds to a cell in the table. The features are labeled by the name of the central atom of the corresponding scoop (e.g., DHF, MTX), as shown in FIGS. 11(A) and 11(B). In other words, the feature labels refer to the atoms on which the feature scoops were centered.

Specifically, FIG. 11(A) illustrates dihydrofolate, and FIG. 11(B) illustrates methotrexate with atom numbers shown. Inspection of the grouping reveals the features of the designated groups are in fact clustered in the same region of discriminant space. However, rectilinear quantization has its problems. There is no easy way with this method to segregate all of the desired features together in distinct bins.

DHF has 53 atoms, so with scoops located on atomic centers, this results in 53 features. However, 6 features fail to pass the threshold for sufficient non-degeneracy and are removed. For the construction of correspondences between the query and database features, multiple features are generated for scoops in the query molecule (DHF) that lack sufficient asymmetry to define the sense of their internal axes. This results in the addition of 25 more features for DHF, for a total of 72. Of the 56 scoops for MTX, 10 fail to pass the threshold for sufficient non-degeneracy, leaving 46 features. The total number of correspondences without grouping is therefore the product of the number of features in DHF and MTX, or 72*46=3312, as shown in Table V.

Specifically, Table V in FIG. 12 illustrates the distribution of the correspondence cluster sizes for rigid body superposition of the crystal structure of MTX onto that of DHF. In the left column, features were not grouped, all query features were corresponded to all database features. The right column sets forth the functional feature grouping, where only similar features were corresponded. Note that with the functional grouping, the total number of correspondences is only 194. In other words, the total number of correspondences with grouping is only about one twelfth of the number without grouping, resulting in a significant decrease in computer time. While the cluster size distribution suggests that the grouping eliminates a number of those correspondences that went into the large clusters in the all-to-all case, detailed inspection of the individual high-voting clusters shows that the same alignments are produced in both cases.

Therefore, it can be seen that, in spite of its problems, a partitioning of discriminant space may be necessary. A brute force comparison of all query features with all candidate features will likely become prohibitively expensive from a computational perspective when applied to larger problems. Furthermore, examination of the large clusters in the full correspondence case (e.g., see Table V in FIG. 12) indicates that noise from spurious members in these clusters contaminates the average transformation of the clusters. Ill-defined transformations from such clusters lead to alignments where few structural elements are aligned well.

In both groupings, when one passes the clusters to the assembler (which in this case may only apply shape screens and scoring since the molecules are already assembled), essentially the same alignments result. This will not be the case when considering the flexibility of MTX. An important point to emphasize here, is that by injecting relevant knowledge into the feature classification scheme, one arrives at the answer with less work. This point becomes important when larger databases of molecules with more conformational degrees of freedom are considered. This is more than a timing issue: in practice, one often must apply cutoffs and limits to the search. Arriving at an answer efficiently at a small scale may sometimes translate into whether one sees it at all at a larger scale.

A result that is fairly robust with respect to choice of clustering parameters is the production of two alignments, one where the benzamide rings are aligned, and the other with the observed crystallographic alignment of the pteridine rings indicating superposition of the regions of the molecules that bind to DHFR. The presence of these two alignments stems from two origins in conflict. One alignment arises from the strength of an exact substructural match, namely the p-aminobenzamide. The other, which is the experimentally observed alignment of the pteridine rings, is due to the similarity in locations of chemical functional groups.

Balancing how exact substructural matches should be weighted with respect to similarity in functional group definition is an issue that must be dealt with in any superposition algorithm or similarity scoring function. Exact substructure matches are sometimes relevant, even if trivial. One certainly could not fault an algorithm for scoring such a correspondence high. Rather, one must balance the relative importance exact substructural matches have with respect to similar substructures. Since there is no universal answer, this should be addressed by the context. In this case (e.g., DHF and MTX), the two form separate and distinct clusters in transformation space, and are thus presented as alternative alignments.

Flexible Superposition

To query DHF against a database that represents the full conformational space of MTX, the MTX structure was fragmented, and the conformations of each fragment and fragment pair were tabulated. The fragmentation is illustrated in FIG. 2, which also shows that the conformational resolution was 60° for the five single bonds and 180° for the aniline bond. Fragment conformers and fragment pairs that are produced using these angle resolutions were analyzed for the presence of non-bonded atom pairs that are closer than 1.7 Å, and these conformations were eliminated from the tabulation (Note that the value of 1.7 Å chosen for the bump check parameters used in this work is rather small. Therefore, some high energy conformations are used as fragment pairs and also some high energy candidates are produced during assembly. The value was chosen to screen out only the worst cases of steric overlap in order to assess the method with a larger work load. The performance of the method improves if this parameter is increased.).

The non-bonded atom threshold reduces the number of conformers of fragment C from 36 to 27, the number of A-B fragment pairs from 72 to 48, and the number of B-C fragment pairs from 324 to 234. The list of inter-fragment torsion angles is appended to the original angle present before fragmentation. The results are shown in Table VI in FIG. 13.

Specifically, Table VI shows the statistics for the fragment and fragment pair partitioning of MTX. The 35 fragment conformers and 284 rotatable bond edge records allow for the representation of more than 15,500 full molecular conformations (e.g., see equation (1)). Thus, one of the 49 A-B fragment pairs and one of the 235 B-C fragment pairs has the original angle found in the crystal structure.

The cluster distributions in Table VII in FIG. 14 show the importance of injecting relevant context into the classification scheme. Specifically, Table VII shows the distribution of the correspondence cluster sizes for flexible superposition of MTX onto the crystal structure of DHF. The middle column refers to features that were grouped according to the element of the atom at the center of the scoop (e.g., C, O or N). The right column refers to features that were grouped according to the chemical function of the molecular region in which the scoop is defined. The two grouping schemes imply different similarity measures. An importance of a cluster is given by the number of its members, a larger number indicating more correspondences consistently supporting the same alignment. The total number of correspondences following from function grouping is only about half the number of correspondences from elemental grouping, which results in a significant decrease in workload by the clustering algorithm.

Thus, as can be seen from the total number of correspondences constructed in each case, the work load of the correspondence step is markedly higher for the elemental grouping scheme than in the functional grouping scheme. Inspection of the partitioning of the elemental grouping revealed a decidedly less rational distribution. Bins were occupied with more random groupings of features compared to the functional scheme.

Furthermore, there is a difference in the types of alignments of the fragment pairs containing the p-amino-benzamide ring and the pteridine ring that are produced by the two scheme. In the functional grouping scheme we see three types of alignments: one with the p-amino-benzamide ring of MTX tightly aligned onto that of the DHF; one with the pteridine ring of MTX tightly aligned onto that of DHF in a way compatible with the DHFR binding implied by the crystal structures; and one with the pteridine ring of MTX tightly aligned onto that of DHF in a way compatible with good steric overlap of the rings.

In contrast, with the element grouping scheme we see only alignments where the p-amino-benzamide ring of MTX is tightly aligned onto that of the DHF. With the set of parameters shown in Table III of FIG. 8, tight alignments of the pteridine rings are not observed, although they can be produced by varying the parameters of the clustering. Not surprisingly, it appears that with the element grouping scheme, the ability to recognize an exact substructural match on the p-amino-benzamide ring is greater than the ability to recognize either a functional group or steric match of the pteridine rings.

It should be added, however, that even with the element grouping scheme, although alignments based on superposition of the pteridine ring of MTX onto that of DHF are not observed, both the binding mode and steric overlap orientations of the pteridine ring can be seen. However, these alignments are produced by correspondences from regions of the molecules away from the pteridine ring and happen to survive shape screening in the assembly phase.

All clusters with votes of five or more are used to produce the starting bases of the assembly step. Since, for this example, completed molecules of MTX are produced when two fragment pairs are merged, the assembly phase completes after one iteration.

Table VIII in FIG. 15 shows the work load of the different phases of the assembly process. Specifically, Table VIII shows the number of bases that survive each assembly phase for the flexible superposition of MTX onto the crystal structure of DHF. The assembly step constructs candidate alignments from the local fragment pair alignments. For both grouping schemes, all clusters with five or more votes are considered for the assembly. Therefore, while the work load is similar for the two grouping schemes, it will turn out that the quality of the produced candidate is better with the functional grouping scheme.

Figure 16:
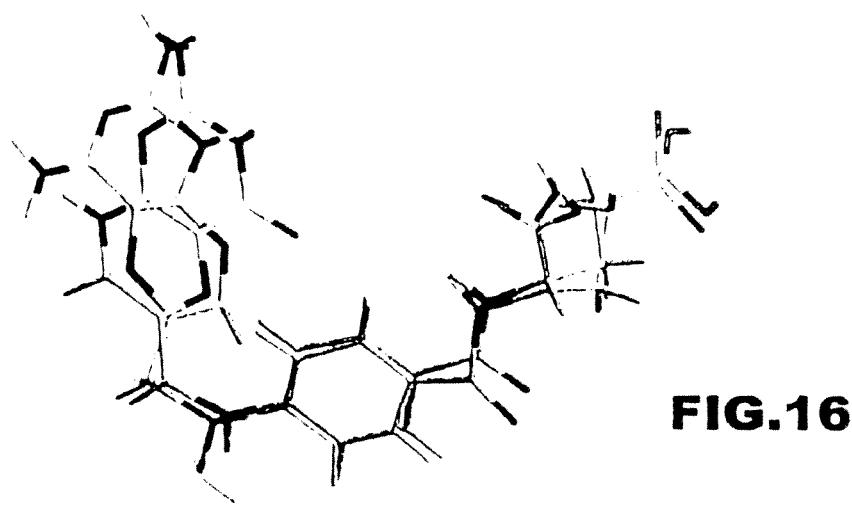
FIG. 16 illustrates a flexible alignment of methotrexate onto the crystal structure of dihydrofolate generated by the inventive system 100.
Figure 17:
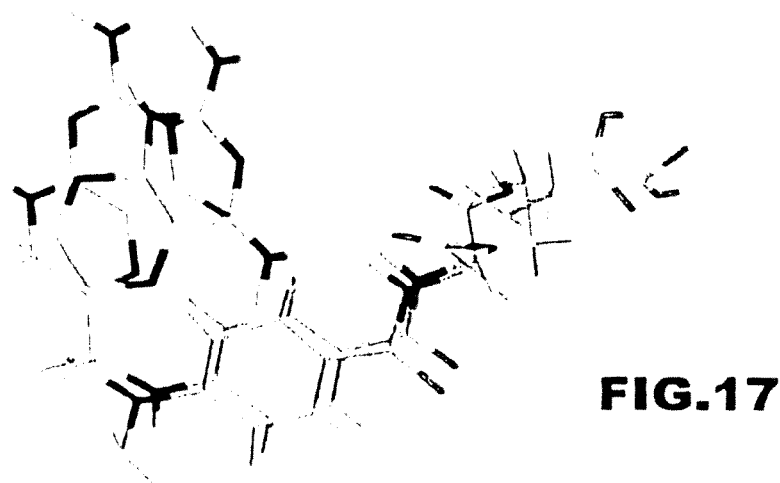
FIG. 17 illustrates a flexible alignment of methotrexate onto the crystal structure of dihydrofolate where the pteridine ring is flipped by 180°, which was generated by the inventive system 100.
Figure 18:
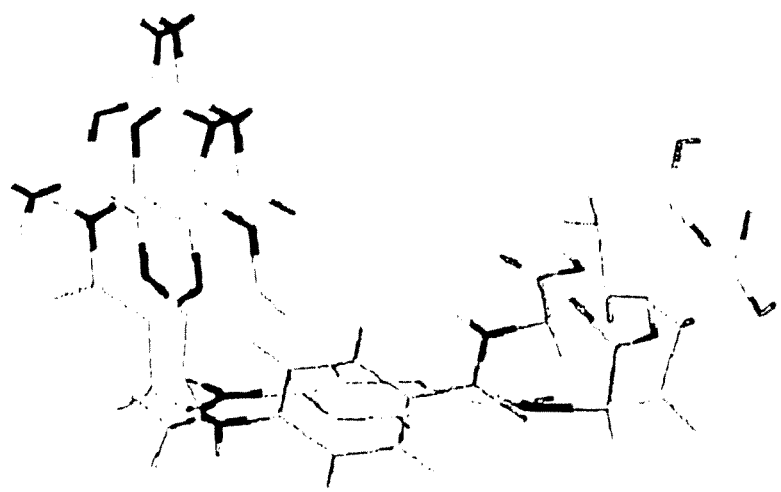
FIG. 18 illustrates a flexible alignment of methotrexate onto the crystal structure of dihydrofolate where the aromatic rings are skewed with respect to each other, which was generated by the inventive system 100.

The assembly phase produced 428 candidate alignments with the element grouping scheme and 436 with the functional grouping scheme. All alignments were scored using the function of equation (32) and clustered into sets based on similarity of score and visual appearance. The scores ranged from 0.40 to 0.75. FIGS. 16-18 show three notable alignments from the three highest scoring sets formed from the 436 alignments that resulted from using the functional grouping scheme.

Specifically, FIG. 16 shows a flexible alignment of MTX onto the crystal structure of DHF generated with the inventive system 100. Most of the feature correspondences that led to this alignment are around the aromatic rings. Therefore, this substructure is almost exactly aligned. The conformation of MTX is different from the one found in the crystal structure. Thus, using the scoring function from equation (32), FIG. 16 shows the highest scoring of the 436 alignments, with a score of Q=0.75.

Further, as shown in FIG. 16, the p-amino-benzamide rings are strongly aligned and the aliphatic chains are actually aligned more closely than is found from the two crystal structures. It is interesting to speculate about why the chains were not observed in this conformation in the crystal structures. Perhaps it can be attributed to the fact that 4dfr is an E. Coli form and 1dhf is the human form of DHFR, and the two sequences differ in a nontrivial way, resulting in a different site geometry. Another reason might be that these chains are solvent exposed, and are thereby influenced by packing interactions from crystallization of the complex. Of course, these kinds of considerations do not factor into a superposition analysis because the enzyme is not considered.

While the alignments represented in FIG. 16 and FIG. 17 both strongly align the p-amino-benzamide rings, the pteridine rings are in opposite orientations. In FIG. 16, the pteridine alignment is indicative of the observed binding, whereas in FIG. 17, with a score of Q=0.63, the pteridine rings are in a sterically similar orientation.

Specifically, FIG. 17 also shows a flexible alignment of MTX onto the crystal structure of DHF, which is mainly based on the aromatic ring substructure match. In contrast to FIG. 16, where the pteridine ring alignment agrees with the crystal structure, here the pteridine ring is flipped by 180°.

Further, due to the strong effect the benzamide has on the average transformation that aligned the respective fragment pairs, the correct hydrogen bonding groups on the pteridine ring are not as incident to the corresponding groups on DHF as they are in the alignment shown in FIG. 18, with a score of Q=0.62.

Specifically, FIG. 18 shows a flexible alignment of MTX onto the crystal structure of DHF generated with the inventive system 100, which is based on a similarity match of the pteridine ring, and it is the one closest to that implied by comparison of the two crystal structures. Note that this is not a substructure match. The planes of the aromatic rings are skewed with respect to each other. Of the three alignments shown, this one has the best overlap of the pteridine ring, and is reasonably close to the observed binding. This favorable pteridine ring alignment comes at the cost of the overlap of the benzamide ring.

The alignments produced by the element grouping scheme were similar to those shown in FIG. 16 and FIG. 17.

Selectivity

It is important to consider how well the inventive system 100 works using these operating parameters when other molecules are added to the database. Two groups of molecules will be added to the database: a group of DHFR inactives and a second group of DHFR inhibitors. By comparing the selectivity of MTX to the eight DHFR inactives the inventors first examined selectivity in a broad context. Examination of selectivity in a finer context will be conducted by comparing MTX to the eight DHFR inhibitors.

Table IX in FIG. 19 gives fragmentation statistics about the sixteen additional molecules that were added to the database containing MTX. The set for this experiment is comprised of eight inhibitors of DHFR and eight inhibitors of other enzymes indicated below, referred to collectively as the DHFR mactives. The eight DHFR inhibitors are labeled according to the compound number in Crippen's original work (G. M. Crippen, "Quantitative Structure Activity Relationships by Distance Geometry: Systematic Analysis of Dihydrofolate Reductase Inhibitors", J. Med. Chem., 23:599, 606, 1980).

Figure 20:
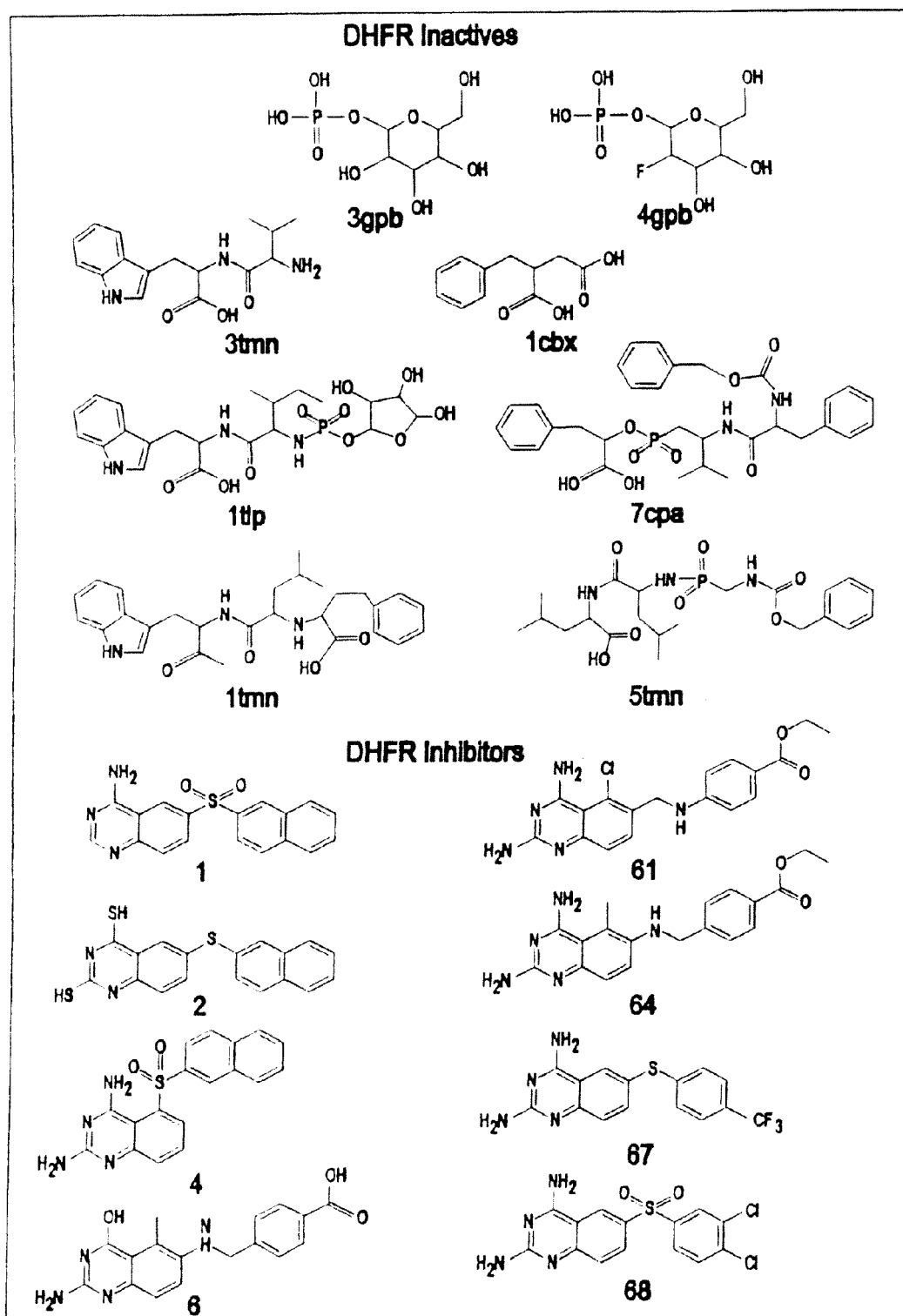
FIG. 20 illustrates sixteen additional structures added to the database containing methotrexate, in the inventors' experiments.

The initial coordinates for the eight DHFR inhibitors shown in FIG. 20 were obtained by energy minimization (The initial structures were generated using the user interface of the inventive system 100 and were Energy-minimized using the Dreiding force field (S. L. Mayo, B. D. Olafson, and W. A. Goddard III, Dreiding force field, J. Phys. Chem., 94:8897, 1990) with the Mulliken suite of programs (Mulliken 2.0: J. E. Rice, H. Horn, B. H. Lengsfield III, A. D. McLean, J. T. Carter, E. S. Replogle, L. A. Barnes, S. A. Maluendes, G. C. Lie, M. Gutowski, W. E. Rudge, P. A. Sauer, R. Lindh, K. Andersson, T. S. Chevalier, P.-O. Widmark, D. Bouzida, J. Pacansky, K. Singh, C. J. Gillan, P. Carnevali, W. C. Swope, B. Liu, IBM Almaden Research Center, San Jose, Calif., 1996).

Specifically, FIG. 20 shows the sixteen additional structures added to the database containing MTX. Each of the DHFR inactives structures were extracted from the PDB source file indicated (e.g., the eight DHFR inactives are ligands whose coordinates were extracted from PDB files of the ligand bound to a protein). Four are Thermolysin inhibitors (from the PDB files 1tlp, 1tmn, 3tmn, 5tmn), two are Carboxypeptidase inhibitors (1 cbx, 7 cpa), and the remaining two are Glycogen Phosphorylase inhibitors (3gpb, 4gpb).

Though small, this group exhibits important features. The size on the inactive range from the small and rigid sugars that are Glycogen Phosphorylase inhibitors, to the larger flexible Thermolysin inhibitors. The size of the eight DHFR inhibitors are consistently smaller than MTX, and their activity spans a wide range (G. M. Crippen, Quantitative structure activity relationships by distance geometry: Systematic analysis of dihydrogolate reductase inhibitors, J. Med. Chem., 23:599 606, 1980), as shown in the last column of Table X in FIG. 21.

Specifically, FIG. 21 shows each molecule's distribution of correspondence cluster sizes for fragment pair alignments. Selectivity for MTX with respect to the eight DHFR inactives is illustrated. This is a direct consequence of the choice of property field and contextual scaling provided by the functional grouping scheme. Selecting the highest ranking transformation clusters, such as all those with at least six correspondences, across all molecules almost exclusively selects MTX (4dfr) for assembly.

Using a torsion angle resolution consistent with the methotrexate characterization described above, the number of conformations represented ranges from a few dozen to over 10 million for the DHFR inactives. The number of conformations represented for the DHFR inhibitors total under a thousand for the set, due to their limited flexibility. Thus, with a fairly small set of molecules, the inventors created a virtual conformational database where the DHFR inhibitors are highly under-represented.

The inventors used the same conditions as were described above (e.g., "Example: Application of the Present Invention to Dihydrofolate and Methotrexate"). All single bonds were sampled at 60° intervals. Terminal groups such as carbody, isopropyl, and phenyl were left rigid. Amides were left in a trans configuration. All property field settings were used as specified in Table III in FIG. 8.

Ligands from 1tlp, 1tmn, 7 cpa, and 5tmn were partitioned into four fragment nodes; and the ligands from 3tmn, 1cbx, 3gpb, 4gpb, and the eight DHFR inhibitors were partitioned into two fragment nodes.

It should be noted that the atom numbering for the non-hydrogen atoms was kept the same as in the corresponding pdb files. For the nine molecules studied, the bonds that were cut to define fragments are as follows (pdb label: {(atom number)-(atom number), ... }): 1cbx: {3 5}, 1tlp: {1 2, 15 16, 23 24}, 1tmn: {1 13, 14 15, 22-25}, 3tmn: {8-9}, 5tmn: {12-13, 17-18, 24-25}, 7 cpa: {9-10, 18-41, 23 26}, 3gpb: {1 7}, 4gpb: {1 7}, and 4dfr: {11 12, 24 25}. The internal torsional angles that were rotated are as follows: 1cbx: {2-3, 5-6}, 1tlp: {2-12, 16 17, 16 19, 27 28, 24 27} 1tmn: {1 2, 2 3, 13 14, 14 17, 21 22, 25 26}, 3tmn: {12-13, 9-12, 2-3}, 1tmn: {3-4, 11-12, 16-17, 17-20, 25-28}, 7 cpa {23 24, 36 41, 18 40, 10 11, 10 39, 2 32}, 3gpb: {5 6}, 4gpb: {5 6}, and 4dfr: {9-13, 14-19, 25-29, 29-30}. All angles were sampled at 60° with the exception of 14 19 in 4dfr, which was sampled at 180°. For the additional DHFR eight inhibitors, the structural parameters of C—S—C groups in molecules 2 and 67 were constrained to the experimental values of CS bond lengths and CSC bond angles in dimethylsulfide. Structural parameters of C—SO$_2$—C groups in molecules 1, 4 and 68 were constrained to the experimental values of CS and SO bond lengths and CSC, CSO and OSO bond angles in dimethylsulfone (David R. Lide, Cre handbook of chemistry and physics, 75.sup.th edition, 1994. pg. 9-31).

The fragmentation statistics for the sixteen molecules are shown along with those for methotrexate in Table IX in FIG. 19. In this table, except for methotrexate (4dfr) the approximate number of conformers represented is simply the number of torsional angles represented for each bond (in this case 6, since the torsional angle resolution is 60°) raised to the number of rotatable bonds. Ethyl groups in esters 61 and 64 where held fixed in an extended conformation. For methotrexate statistics, see the above discussion in Table VI (FIG. 13) and Equation (1). Note that this represents only approximately the number of conformers because some, sterically forbidden, are removed by the bump check, and others are added, corresponding to the inter-fragment torsion angles present in the original crystal or energy minimized structures.

The number of fragment pairs is the number that have passed a bump check of 1.7 Å. Features were computed at each atom center for each fragment pair. One can see from the data in the table that there are considerable savings in breaking the larger structures up and characterizing fragment pairs rather than molecular conformations. Due to the single partitioning of the DHRF inhibitors, only the bump checks reduced the number of fragment pairs used for feature extraction.

Feature computation can be expensive, but it may only have to be performed once, when molecular information is added to the database. Its cost will vary widely depending on complexity of the field computation and grid resolution, if the field is computed on a grid. Once the features are computed, however, timings for the alignment and assembly stages of a query are independent of the field complexity. Feature computation with the property field as discussed above, and operational settings averaged about 4 features on a workstation (The timings were produced running the program of an IBM RS/6000 43P Model 260 workstation, which has a Power3 CPU running at 200 and a 4 MB L2 Cache).

Selectivity During Alignment Stage

It is important for the efficiency and scalability of the method that the burden on the assembly stage is kept to a minimum. The results shown in Tables X, XI, XII and XIII (FIGS. 21-24, respectively) indicate a considerable degree of selectivity before the assembly stage for MTX and the eight DHFR inhibitors relative to the DHFR inactives. The feature classification scheme selects which correspondences will be made. There are a total of 542,981 features in the database, and 72 features on the query molecule. This gives 39,094,632 possible correspondences. Using the functional grouping scheme, and screening out degenerate features, only 1,421, 086 or about 3.7% of the total possible correspondences, were considered for MTX and the eight inactives.

If the other eight inhibitors are included, this number only rises to 1,458, 843. The correspondences of MTX and the eight inhibitors are only 0.19% of the total. Each correspondence has an associated transformation which is clustered as described above. Clustering produced 1,053,312 transformation clusters in total. These transformation clusters are ranked according to the number of correspondences they contain. From this pool of transformation clusters, each of which describes a fragment pair aligned on the query molecule, one can select for assembly either the top ranking clusters from each molecule, or the top ranking clusters from the entire pool of clusters. For either choice, one sees a high degree of selectivity for MTX, which has been achieved by the choice of property field and functional grouping scaling scheme.

Figure 25:
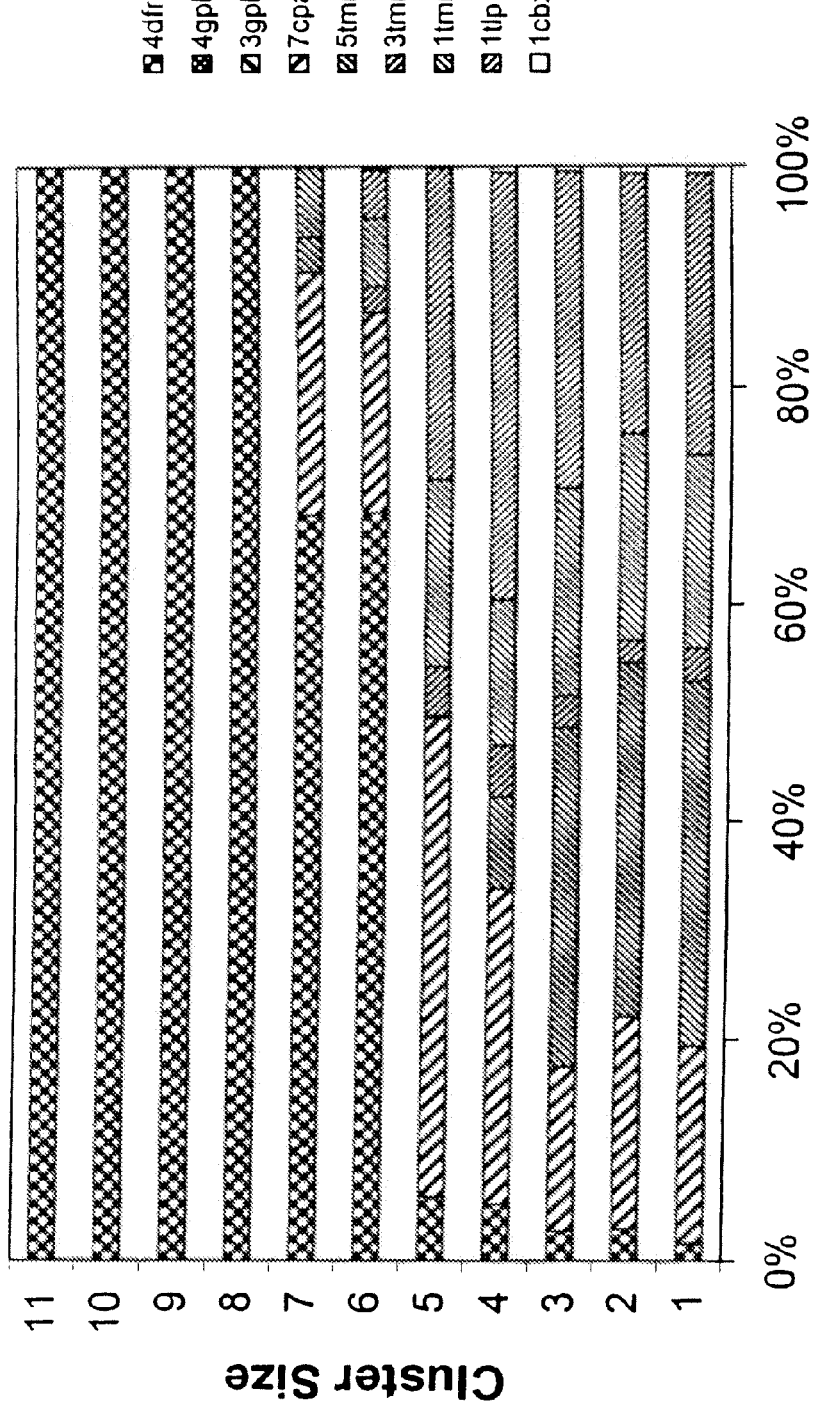
FIG. 25 is a bar graph showing the percentage of clusters by molecules for each cluster size.

Table X (FIG. 21) and FIG. 25 illustrate the selectivity of DHF for MTX with respect to the eight inactives in the database. Table X shows each molecule's distribution of correspondence cluster sizes for alignments of its fragment pairs onto DHF. Selectivity for MTX with respect to the eight DHFR inactives is illustrated. This is a direct consequence of the choice of property field and contextual scaling provided by the functional grouping scheme. Selecting the highest ranking transformation clusters, such as all those with at least six correspondences, across all molecules almost exclusively selects MTX (4dfr) for assembly.

FIG. 25 gives the corresponding proportions from each of the eight inactives and MTX for each cluster size. Specifically, FIG. 25 is a 100% stacked bar chart, derived from Table X in FIG. 21, for the proportion of transformation clusters for each cluster size for each of the eight inactives and MTX (4dfr). One sees that for small cluster sizes transformations of fragment pairs from MTX represent a small fraction of the total number of cluster of that size. For the larger clusters, however, transformations involving MTX dominate. Selecting the largest clusters for assembly, therefore, almost exclusively focuses resources on MTX.

As shown in FIG. 21, excluding the set of eight DHF inhibitors, there were 1,421,086 feature correspondences. Only 35,037, or 2.5% of them were from MTX. Similarly, this gives 1,036,401 transformation clusters, of which only 20,451, or 2.0% were from MTX. However, if one considers only the larger clusters, which represent more significant alignments, one sees that MTX quickly dominates the distribution. For example, if one selects clusters with six or more transformations from the entire pool of transformations, MTX represents 405 of the 533, or 76%; seven or more gives 170 out of 190 or 89%; and eight or more exclusively selects MTX.

Thus, even though MTX represents a small fraction of the total correspondences considered, clustering clearly reveals MTX fragment pairs as the best ones to use in the assembly stage. Subsequent assembly of these MTX fragment pairs leads to the results seen in the previous sections. The additional 23 million conformations represented by the 13 thousand fragment pairs of the molecules in FIG. 20 do not affect the result that MTX is primarily selected from the database.

Table XI in FIG. 22 shows the corresponding results for the DHFR inhibitors. Specifically, Table XI illustrates selectivity for the DHFR inhibitors with respect to DHFR inactives by comparison with Table X (FIG. 21). Note that although correspondences involving the inhibitors form larger clusters than inactives, such correspondences are still less favored than MTX (4dfr). Inspection reveals that clusters greater than 6 are mainly due to the alignment of the flexible chain and benzamide groups. This part of DHF and MTX is mostly solver exposed, as seen in the crystal structures. Corresponding structure that would have occupied the same space is not present in the eight inhibitors.

Further, as seen in Table XI, despite the low number of conformations relative to the inactives, the DHFR inhibitors scored consistently high and were within the selection threshold of 6 votes of higher. A threshold of 6 or more reduces the number of alignments for consideration to 606,478 of which are from the inhibitor set (including MTX). Even with a threshold of 5 votes or higher, the number of alignments to consider is 5,221, 1, 031 being from the inhibitor set. This is out of the 1,061,703 total clusters.

Selection of the larger clusters for assembly therefore appears to be a valid means of significantly reducing the aligned fragment pairs prior to assembly. Given the elementary level of consideration for medicinal chemistry, the dramatic reduction in the number of clusters to consider is encouraging. It is clear that such specific pre-screening is essential for larger datasets, particularly when the final scoring function used is expensive.

Selectivity During Assembly Stage

If, however, the top ranking transformation clusters from each molecule are considered individually, it is interesting to see whether there will still be selectivity for MTX. Table XII in FIG. 23 shows the timing and load data for the assembly of the fragment pairs MTX and the eight inactives. Specifically, Table XII shows the alignment and assembly timings (The timings were produced running the program of an IBM RS/6000 43P Model 260 workstation, which has a Power3 CPU running at 200 MHz and a 4 MB L2 Cache), the top Carbo scores, and the total number of candidates for each ligand investigated. The statistics are for the case of flexible alignment of the eight inactives and MTX onto the DHF query molecule. The initial alignments for each molecule represent those from the largest clusters.

Table XIII in FIG. 24 gives the data for the eight inhibitors. Specifically, Table XIII shows the alignment and assembly timings (As in Table XII, here the timings were produced running the program of an IBM RS/6000 43P Model 260 workstation, which has a Power3 CPU running at 200 MHz and a 4 MB L2 Cache), the top Carbo scores, and the total number of candidates for the eight DHFR inhibitors investigated. All structures in this series had only one fragment pair, so no merging was required. The last column on the right is the experimental binding energy.

Based on the size of the transformation clusters, the top ranking fragment pair alignments were selected for each molecule separately. For each molecule, enough cluster sizes were considered to yield at least 500 fragment pair alignments. This resulted in the number of initial alignments shown in Table XII (FIG. 23) and Table XIII (FIG. 24).

Thus, it can be seen that the bulk of the time for the Thermolysin and Carboxypeptidase inhibitors is spent indexing features and clustering transformations during the alignment stage, where most of the potential assembly load is screened out. For MTX, however, most of the time is spent on assembly due to the large number of fragment pair alignments that could be merged, screened for shape and scored. All assembly runs were exhaustive for the selected fragment pairs.

The assembly results again strongly favor MTX over any of the other molecules investigated. Most of the molecules did not have sufficient similarity to DHF for a complete assembly of the molecule. In fact, only MTX showed any merges of fragment pairs. For those molecules that had opportunities to merge, fragment pairs must be placed such that the common fragments are proximal enough to be merged. For molecules where only a small part is similar to the DHF query, the assembly stage will yield as candidates the fragment pairs or partial assemblies aligned to the corresponding query regions. This is the case in Table XII (FIG. 23) and all of Table XIII (FIG. 24) where molecules without any counted merges still produced candidates. Assembling complete conformers requires the combination of high ranking fragment pairs and their proximal placement.

Alignments must also pass a shape screen in order to qualify as candidates and be scored. One can see from Table XII (FIG. 23) that for three of the molecules, not only were there no merges of fragment pairs, but none of the initial alignments were sufficiently contained within the volume of the query molecule to make it past the shape screen. Thus, despite the flexibility of these molecules, only a small number of candidates were submitted for scoring. Table XIII (FIG. 24) shows all of the eight inhibitors had alignments of conformers that passed the shape screen.

The last column of Table XII (FIG. 23) shows the highest Carbo scores of the candidates produced by the assembly stage. It can be seen, however, that of the few candidate conformer alignments submitted for final evaluation, the Carbo score ranks MTX well above the other. The four molecules from 3tmn, 1cbx, 3gpb, and 4gpb are complete as a single fragment pair, and so no assembly is required. Their difference in size and shape from DHF results in a much lower Carbo score. It should be emphasized here that there except for MTX and these four molecules, and the eight inhibitors, the Carbo scores represent the evaluation of alignments of partially assembled molecules.

Inspection of the alignments of the DHFR inhibitors reveal that in each case, the binding mode corresponding to MTX is observed (e.g., see FIGS. 16, 17 and 18). Compounds 2 and 6 have an Hbond acceptor that allows a binding mode analogous to DHF, which is observed. In each case the top alignments are adequately placed to relax into a corresponding binding mode.

As noted above, Table XIII (FIG. 24) shows the assembly results for the set of eight DHFR inhibitors. They are represented by a single fragment pair due to their limited flexibility, so no merging step was required. The shape screen was the only checkpoint that was applied to the inhibitors. Since the shape evaluation is simply the Carbo score, no considerations relevant to medicinal chemistry beyond shape were made for this example (e.g., consideration of functional group compatibility, as in SQ (Michael D. Miller, Robert P. Sheridan, and Simon K. Kearsley, "Sq: A Program for Rapidly Producing Pharmacophorically Relevant Molecular Superpositions", *J. Med. Chem.*, 42:1505-1514, 1999)).

One of the alignments of 3tmn has a Carbo score of 0.54. This is the only compound with a comparable Carbo score to the DHFR inhibitors. Inspection of this alignment, however, reveals that 3tmn is aligned to the branched chain of DHF. Again, this could well be screened out by filters favoring the known binding mode of DHFR inhibitors, since the branched chain region is known from crystal structures to be solvent exposed. This is also the case with the alignments observed with the sugars 3gpb and 4gpb.

A further note on the lower scores of the DHFR Inhibitors is that the Carbo score penalizes for any mismatched shape. When aligned correctly to DHF, the DHFR inhibitors have no corresponding structure to fill the volume corresponding to the chain of DHF. This is reflected in the scores of the best alignments, which are around 0.5.

Even though the inventors selected the top ranking fragment pair alignments for each molecule, fragment pairs did not match across the entire volume of the query, so there were not multiple fragment pairs to be considered for merging to form more complete conformers (and, therefore, higher scoring candidates) for molecules other than MTX.

The structure of DHFR was not used at any phase of the screening process, since this is a similarity searching application. It is not our intention here to further refine or optimize the binding mode. Our results show that from a modest flexible dataset, we are able to reduce the number of conformation and alignments to a few hundred, from several million.

In summary, the inventive system 100 offers a systematic way to use arbitrary property fields for the purposes of similarity search and alignment. Context specific information can be used to scale the relative importance of high dimensional descriptors derived from the property field under study. The system 100 may be designed to operate on overlapping parts, or fragment pairs, of molecules, and utilizes an efficient method of conformational space representation.

The inventors applied the inventive system 100 to the benchmark dihydrofolate-methotrexate system, and have demonstrated that by injecting context specific knowledge into the feature classification scheme, one arrives at the reasonable alignments more efficiently. For this study, the inventors used a very simple property field. Even with this simple property field the appropriate inclusion of context in the definition of similarity allowed the production of alignments consistent with the binding modes present in the crystal structures in both rigid and flexible treatments of conformational space.

Further, the inventors looked in detail at how the inventive system 100 works in performing a query for alignments on dihydrofolate from a database of seventeen molecules representing approximately 23 million conformations. The inventive system 100 exhibits a high degree of selectivity for alignments of methotrexate and as well as other DHFR inhibitors. The selectivity is apparent at initial alignment and assembly stages, and is reflected in the resulting Carbo scores.

Figure 26:
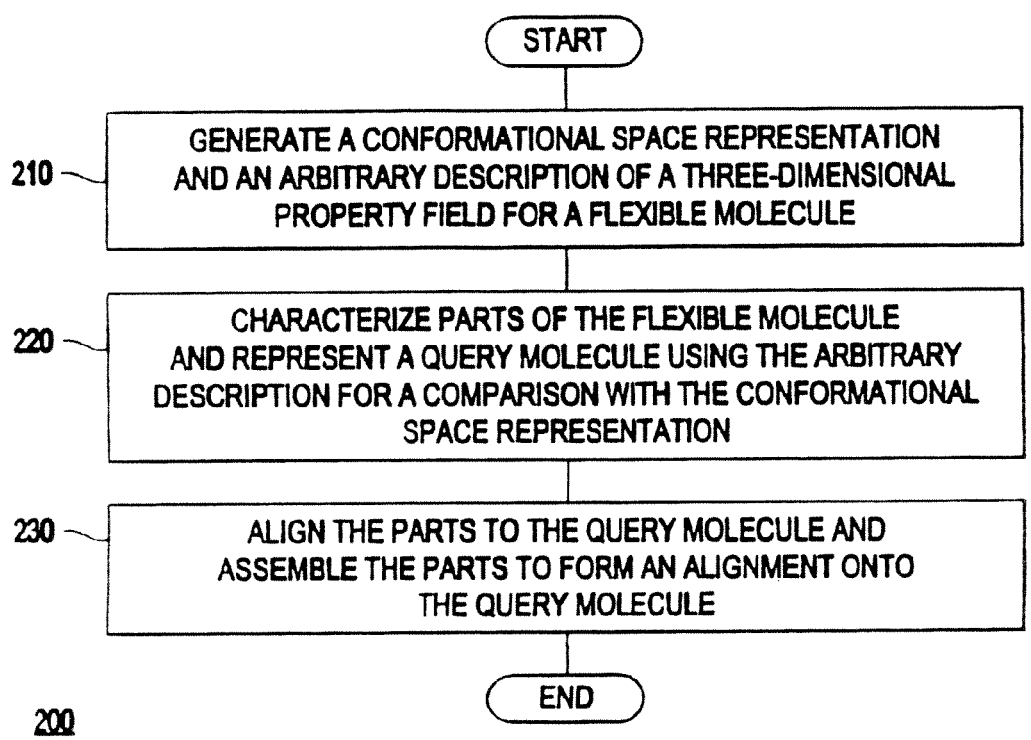
FIG. 26 is a flow chart illustrating an inventive field-based similarity search method 200 according to the present invention.

Referring again to the drawings, FIG. 26 illustrates an inventive field-based similarity search method 200 according to the present invention. As shown in FIG. 26, the inventive method 200 includes generating (210) a conformational space representation and an arbitrary description of a three-dimensional property field for a flexible molecule, characterizing (220) parts of the flexible molecule and representing a query molecule using the arbitrary description for a comparison with the conformational space representation, and aligning (230) the parts to the query molecule and assembling the parts to form an alignment onto the query molecule.

Figure 27:
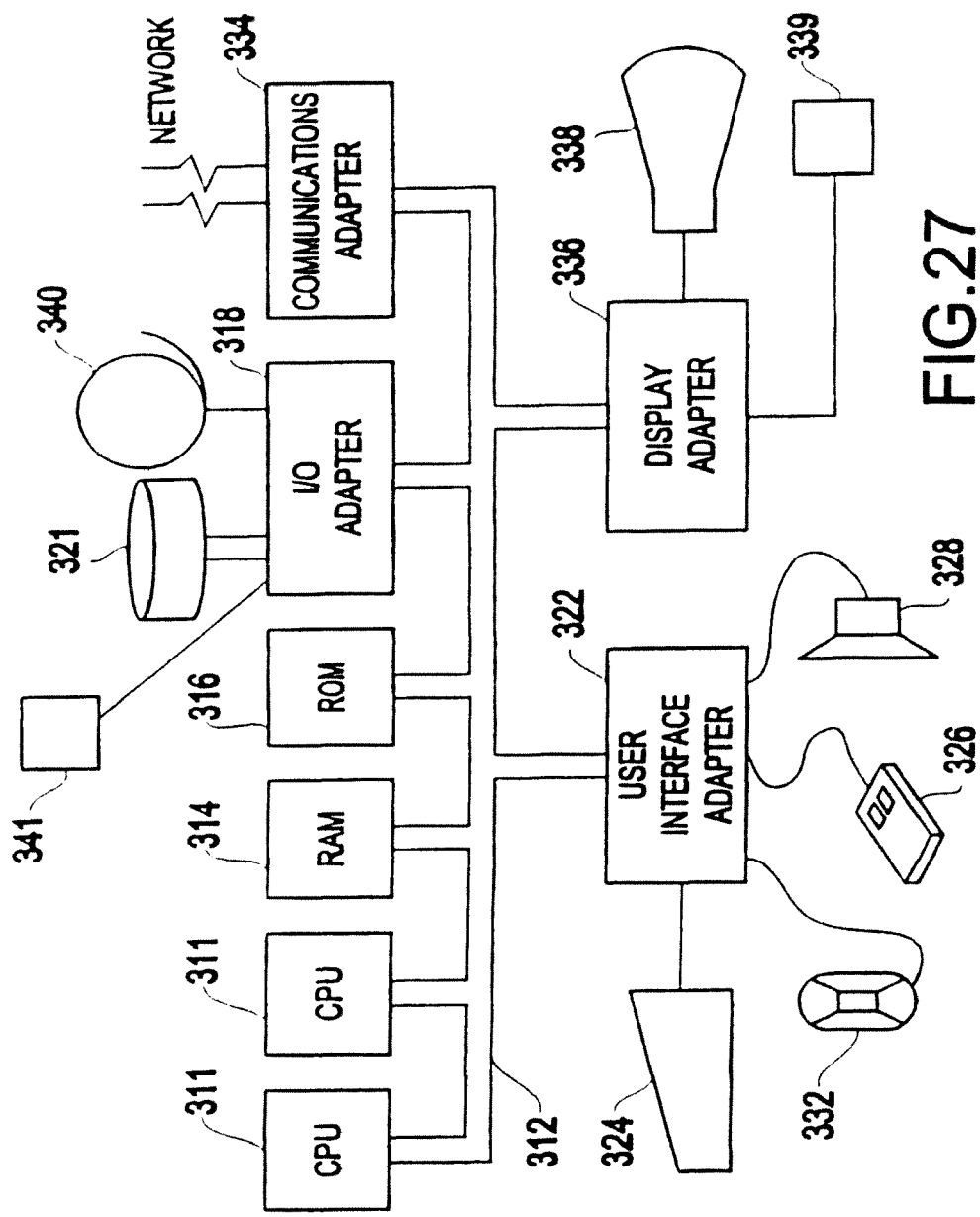
FIG. 27 illustrates a typical hardware configuration 300 which may be used for implementing the inventive field-based similarity search system and method according to the present invention.

Referring again to the drawings, FIG. 27 illustrates a typical hardware configuration which may be used for implementing the inventive field-based similarity search system and method. The configuration has preferably at least one processor or central processing unit (CPU) 311. The CPUs 311 are interconnected via a system bus 312 to a random access memory (RAM) 314, read-only memory (ROM) 316, input/output (I/O) adapter 318 (for connecting peripheral devices such as disk units 321 and tape drives 340 to the bus 312), user interface adapter 322 (for connecting a keyboard 324, mouse 326, speaker 328, microphone 332, and/or other user interface device to the bus 312), a communication adapter 334 for connecting an information handling system to a data processing network, the Internet, and Intranet, a personal area network (PAN), etc., and a display adapter 336 for connecting the bus 312 to a display device 338 and/or printer 339. Further, an automated reader/scanner 341 may be included. Such readers/scanners are commercially available from many sources.

In addition to the system described above, a different aspect of the invention includes a computer-implemented method for performing the above method. As an example, this method may be implemented in the particular environment discussed above.

Such a method may be implemented, for example, by operating a computer, as embodied by a digital data processing apparatus, to execute a sequence of machine-readable instructions. These instructions may reside in various types of signal-bearing media.

Thus, this aspect of the present invention is directed to a programmed product, including signal-bearing media tangibly embodying a program of machine-readable instructions executable by a digital data processor to perform the above method.

Such a method may be implemented, for example, by operating the CPU 311 to execute a sequence of machine-readable instructions. These instructions may reside in various types of signal bearing media.

Thus, this aspect of the present invention is directed to a programmed product, comprising signal-bearing media tangibly embodying a program of machine-readable instructions executable by a digital data processor incorporating the CPU 311 and hardware above, to perform the method of the invention.

Figure 28:
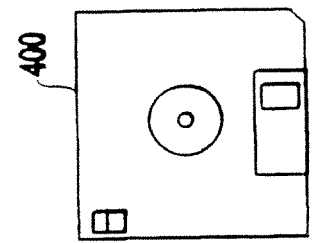
FIG. 28 illustrates a signal-bearing media 400 for storing instructions for performing the inventive field-based similarity search method according to the present invention.

This signal-bearing media may include, for example, a RAM contained within the CPU 311, as represented by the fast-access storage for example. Alternatively, the instructions may be contained in another signal-bearing media, such as a magnetic data storage diskette 400 (FIG. 28), directly or indirectly accessible by the CPU 311.

Whether contained in the computer server/CPU 311, or elsewhere, the instructions may be stored on a variety of machine-readable data storage media, such as DASD storage (e.g., a conventional "hard drive" or a RAID array), magnetic tape, electronic read-only memory (e.g., ROM, EPROM, or EEPROM), an optical storage device (e.g., CD-ROM, WORM, DVD, digital optical tape, etc.), paper "punch" cards, or other suitable signal-bearing media including transmission media such as digital and analog and communication links and wireless. In an illustrative embodiment of the invention, the machine-readable instructions may comprise software object code, complied from a language such as "C," etc.

With its unique and novel features, the present invention provides a fast and efficient field-based similarity search system and method which are not confined to a particular field definition. For example, the inventive system and method may be designed for simplistic, phenomenological fields, as well as for fields derived from quantum mechanical calculations. Therefore, the claimed system and method provides improved versatility over conventional systems and methods.

While the invention has been described in terms of preferred embodiments, those skilled in the art will recognize that the invention can be practiced with modification within the spirit and scope of the appended claims.

What is claimed is:

1. A similarity search method, comprising:
generating a feature database which stores data pertaining to a candidate molecule, as executed by a processor of a computer, said database comprising a hash table having entries which are generated based on:
   a set of descriptors generated from conformations of fragment graphs of said candidate molecule, said fragment graphs including plural fragment nodes connected by rotatable bond edges, a specific conformation of said fragment node comprising a fragment of said candidate molecule, and two neighboring fragments connected by a rotatable bond at a specific dihedral angle comprising a fragment pair; and
   a context-adapted descriptor-to-key mapping which maps said set of descriptors to a set of feature keys comprising indices that label grid cells in discriminant space;
generating scoops, descriptors and keys for a query molecule;
identifying a match between a query molecule fragment pair feature and a candidate molecule fragment pair feature by comparing said keys of said query molecule to said keys in said feature database, a correspondence comprising a scoop for said candidate molecule stored in said feature database having a same key as a scoop for said query molecule;
using said match to align a fragment pair of said candidate molecule to said query molecule by overlaying internal coordinate axes of said scoops for said candidate and query molecules, said correspondence implying an alignment of said candidate molecule and query molecule fragment pairs;
determining the number of candidate molecule fragment pairs the number of candidate molecule fragment pairs in the set, $C_{fp}$, being given by $C_{fp}=(n-1)\cdot(C_{frag})^2\cdot C_{rbe}$, where n is the number of fragments in said candidate molecule and n−1 is the number of rotatable bond edges connecting said n fragments, $C_{frag}$ is the number of conformations in a fragment of said fragments, and $C_{rbe}$ is the number of steps in which said rotatable bond edges are sampled;
assembling the entirety of the fragment pairs of said candidate molecule to form an alignment thereof onto said query molecule;
retrieving a candidate molecule fragment pair having at least a predetermined number of matching features; and
displaying a result of said retrieving said candidate molecule fragment pair.

2. The method according to claim 1, further comprising: storing said query molecule fragment pair feature.

3. The method according to claim 1, further comprising: storing data and instructions to be executed by the processor.

4. The method according to claim 1, wherein said processor identifies said query molecule fragment pair feature.

5. The method according to claim 4, wherein said processor matches a query molecule fragment pair feature with the candidate molecule fragment pair feature.

6. The method according to claim 5, wherein said processor retrieves a candidate molecule fragment pair having at least a predetermined number of matching features.

7. The method according to claim 1, wherein said processor identifies said candidate molecule which is similar to said query molecule by using a context-adaptive descriptor scaling procedure as a basis for similarity.

8. The method according to claim 1, wherein said database stores conformational space representation of said candidate molecule, and an input device inputs a conformational space representation of said query molecule.

9. The method according to claim 1, wherein said processor identifies corresponding features by comparing features of candidate molecule fragment pairs with the features of the query molecule fragment pairs.

10. The method according to claim 1, wherein said scoop of said query molecule comprises a sphere defined by a set of points within or around said query molecule.

11. The method according to claim 1, wherein said features of said candidate molecule fragment pair and query molecule fragment pair comprise generalizations of comparative molecular moment analysis descriptors.

12. The method according to claim 1, wherein an entry of said hash table refers to a fragment pair of said candidate molecule and describes an internal frame associated with a descriptor of said set of descriptors.

13. A method for finding alignments of a flexible molecule to a query molecule. said method comprising:
  representing a conformation space of said flexible molecule;
  generating an arbitrary description of a three-dimensional property field of said flexible molecule;
  characterizing parts of said flexible molecule using said arbitrary description;
  generating a feature database which stores data pertaining to said flexible molecule on a processor of a computer, said database comprising a hash table having entries which are generated based on:
    a set of descriptors generated from conformations of fragment graphs of said flexible molecule, said fragment graphs including plural fragment nodes connected by rotatable bond edges, a specific conformation of said fragment node comprising a fragment of said flexible molecule, and two neighboring fragments connected by a rotatable bond at a specific dihedral angle comprising a fragment pair; and
    a context-adapted descriptor-to-key mapping which maps said set of descriptors to a set of feature keys comprising indices that label grid cells in discriminant space;
  representing a query molecule using said arbitrary description for a comparison with molecules represented by said conformation space by generating scoops, descriptors and keys for said query molecule;
  identifying a match between a query molecule fragment pair feature and a flexible molecule fragment pair feature by comparing said keys of said query molecule to said keys in said feature database, a correspondence comprising a scoop for said flexible molecule stored in said feature database having a same key as a scoop for said query molecule;
  aligning said parts of said flexible molecule to said query molecule by overlaying internal coordinate axes of said scoops for said flexible and query molecules, said correspondence implying an alignment of said flexible molecule and query molecule fragment pairs;
  determining the number of said parts of said number of flexible molecule fragment pairs, the number of said parts of said number of flexible molecule fragment pairs in the set, $C_{fp}$, being given by $C_{fp}=(n-1)\cdot(C_{frag})^2\cdot C_{rbe}$, where n is the number of fragments in said candidate molecule and n−1 is the number of rotatable bond edges connecting said n fragments, $C_{frag}$ is the number of conformations in a fragment of said fragments, and $C_{rbe}$ is the number of steps in which said rotatable bond edges are sampled;
  assembling said parts of said flexible molecule to form an alignment thereof onto said query molecule;
  identifying a flexible molecule which is similar to said query molecule based on a result of said aligning said parts of said flexible and query molecules; and
  displaying a result of said assembling said parts.

14. A non-transitory computer-readable storage medium encoded with a computer program executable by a digital processing apparatus to perform a similarity search method, said method comprising:
  generating a conformational space representation and an arbitrary description of a three-dimensional property field for a flexible molecule;
  generating a feature database which stores data pertaining to a flexible molecule, said database comprising a hash table having entries which are generated based on:
    a set of descriptors generated from conformations of fragment graphs of said flexible molecule, said fragment graphs including plural fragment nodes connected by rotatable bond edges, a specific conformation of said fragment node comprising a fragment of said flexible molecule, and two neighboring fragments connected by a rotatable bond at a specific dihedral angle comprising a fragment pair; and
    a context-adapted descriptor-to-key mapping which maps said set of descriptors to a set of feature keys comprising indices that label grid cells in discriminant space;
  representing a query molecule using said arbitrary description for a comparison with said conformational space representation by generating scoops, descriptors and keys for said query molecule;
  identifying a match between a query molecule fragment pair feature and a flexible molecule fragment pair by comparing said keys of said query molecule to said keys in said feature database, a correspondence comprising a scoop for said flexible molecule stored in said feature database having a same key as a scoop for said query molecule;
  aligning said parts to said query molecule and assembling said parts to form an alignment onto said query molecule by overlaying internal coordinate axes of said scoops for said flexible and query molecules, said correspondence implying an alignment of said flexible molecule and query molecule fragment pairs:
  determining the number of said parts of said number of flexible molecule fragment pairs, the number of said parts of said number of flexible molecule fragment pairs in the set. $C_{fp}$, being given by $C_{fp}=(n-1)\cdot(C_{frag})^2\cdot C_{rbe}$, where n is the number of fragments in said candidate molecule and n−1 is the number of rotatable bond edges connecting said n fragments, $C_{frag}$ is the number of conformations in a fragment of said fragments, and $C_{rbe}$ is the number of steps in which said rotatable bond edges are sampled;
  identifying a flexible molecule which is similar to said query molecule based on a result of said aligning; and
  displaying a result of said aligning said parts.

* * * * *